United States Patent
Last et al.

(10) Patent No.: US 10,723,707 B2
(45) Date of Patent: Jul. 28, 2020

(54) HETEROCYCLIC SUBSTITUTED 2-AMINO QUINAZOLINE DERIVATIVES FOR THE TREATMENT OF VIRAL INFECTIONS

(71) Applicant: JANSSEN SCIENCES IRELAND UNLIMITED COMPANY, Co Cork (IE)

(72) Inventors: Stefaan Julien Last, Lint (BE); David Craig McGowan, Brussels (BE); Werner Embrechts, Beerse (BE); Serge Maria Aloysius Pieters, Ar Hulst (NL); Tim Hugo Maria Jonckers, Heist-op-den-Berg (BE); Pierre Jean-Marie Bernard Raboisson, Wavre (BE)

(73) Assignee: Janssen Sciences Ireland Unlimited Company, Ringaskiddy, CO Cork (IE)

( * ) Notice: Subject to any disclaimer, the term of this patent is extended or adjusted under 35 U.S.C. 154(b) by 0 days.

(21) Appl. No.: 16/377,752

(22) Filed: Apr. 8, 2019

(65) Prior Publication Data

US 2019/0330160 A1 Oct. 31, 2019

Related U.S. Application Data

(63) Continuation of application No. 15/591,473, filed on May 10, 2017, now Pat. No. 10,253,003, which is a continuation of application No. 14/443,305, filed as application No. PCT/EP2013/073901 on Nov. 15, 2013, now Pat. No. 9,663,474.

(30) Foreign Application Priority Data

Nov. 16, 2012 (EP) .................................... 12192970

(51) Int. Cl.
  *C07D 239/84* (2006.01)
  *C07D 239/95* (2006.01)
  *C07D 401/12* (2006.01)
  *C07D 403/12* (2006.01)
  *C07D 413/12* (2006.01)
  *C07D 417/12* (2006.01)

(52) U.S. Cl.
  CPC ......... *C07D 239/84* (2013.01); *C07D 239/95* (2013.01); *C07D 401/12* (2013.01); *C07D 403/12* (2013.01); *C07D 413/12* (2013.01); *C07D 417/12* (2013.01)

(58) Field of Classification Search
  CPC ................................................... C07D 239/84
  See application file for complete search history.

(56) References Cited

U.S. PATENT DOCUMENTS

| | | | |
|---|---|---|---|
| 6,028,076 A | 2/2000 | Hirota et al. | |
| 6,329,381 B1 | 12/2001 | Kurimoto et al. | |
| 6,376,501 B1 | 4/2002 | Isobe et al. | |
| 6,458,798 B1 | 10/2002 | Fujita et al. | |
| 6,503,908 B1 | 1/2003 | Maw | |
| 6,583,148 B1 | 6/2003 | Kelley et al. | |
| 6,951,866 B2 | 10/2005 | Fujita et al. | |
| 7,030,118 B2 | 4/2006 | Lombardo et al. | |
| 7,091,232 B2 | 8/2006 | Chow et al. | |
| 7,498,409 B2 | 3/2009 | Vlach et al. | |
| 7,524,852 B2 | 4/2009 | Arai et al. | |
| 7,531,547 B2 | 5/2009 | Dillon et al. | |
| 7,754,728 B2 | 7/2010 | Isobe et al. | |
| 7,923,554 B2 | 4/2011 | Hoornaert et al. | |
| 8,012,964 B2 | 9/2011 | Kurimoto et al. | |
| 8,022,077 B2 | 9/2011 | Simmen et al. | |
| 8,455,458 B2 | 6/2013 | Marcum et al. | |
| 8,486,952 B2 | 7/2013 | Boy et al. | |
| 8,637,525 B2 | 1/2014 | Boy et al. | |
| 8,916,575 B2 | 12/2014 | McGowan et al. | |
| 9,133,192 B2 | 9/2015 | McGowan et al. | |
| 9,284,304 B2 | 3/2016 | McGowan et al. | |
| 9,365,571 B2 | 6/2016 | McGowan et al. | |
| 9,376,448 B2 | 6/2016 | Charifson et al. | |
| 9,416,114 B2 | 8/2016 | Gembus et al. | |
| 9,422,250 B2 | 8/2016 | McGowan | |
| 9,499,549 B2 | 11/2016 | McGowan et al. | |
| 9,556,176 B2 | 1/2017 | Bonfanti et al. | |
| 9,556,199 B2 | 1/2017 | McGowan et al. | |
| 9,598,378 B2 | 3/2017 | McGowan et al. | |
| 9,663,474 B2 | 5/2017 | Last et al. | |
| 9,878,996 B2 | 1/2018 | Silverman et al. | |
| 10,253,003 B2 | 4/2019 | Last | |
| 2005/0054590 A1 | 3/2005 | Averett | |
| 2006/0258682 A1 | 11/2006 | Liao et al. | |

(Continued)

FOREIGN PATENT DOCUMENTS

CN 101784548 A 7/2010
EP 0882727 12/1998

(Continued)

OTHER PUBLICATIONS

Tomonori, et al., "Ti-Crossed-Claisen Condensation between Carboxylic Ester and Acid Chlorides or Acids: A Highly Selective and General Method for the Preparation of Various Keto Esters", Journal of the American Chemical Society, vol. 127:pp. 2854-2855 (2005).

(Continued)

*Primary Examiner* — Paul V Ward

(74) *Attorney, Agent, or Firm* — Brian C. Trinque; Lathrop GPM LLP

(57) ABSTRACT

This invention relates to heterocyclic substituted 2-aminoquinazoline derivatives, processes for their preparation, pharmaceutical compositions, and their use in treating viral infections.

26 Claims, No Drawings

Specification includes a Sequence Listing.

(56) References Cited

U.S. PATENT DOCUMENTS

| | | |
|---|---|---|
| 2007/0225303 A1 | 9/2007 | Ogrita et al. |
| 2009/0285782 A1 | 11/2009 | Gao et al. |
| 2010/0143299 A1 | 6/2010 | Gao et al. |
| 2014/0073642 A1 | 3/2014 | McGowan |
| 2014/0148433 A1 | 5/2014 | Follmann et al. |
| 2015/0274676 A1 | 10/2015 | McGowan et al. |
| 2015/0284339 A1 | 10/2015 | Last |
| 2015/0299221 A1 | 10/2015 | Bonfanti et al. |
| 2015/0336907 A1 | 11/2015 | Gembus et al. |
| 2016/0304531 A1 | 10/2016 | Bonfanti et al. |
| 2017/0349557 A1 | 12/2017 | Last et al. |

FOREIGN PATENT DOCUMENTS

| | | |
|---|---|---|
| EP | 0899263 A3 | 3/1999 |
| EP | 1552842 A1 | 6/2003 |
| EP | 1110951 A1 | 6/2006 |
| EP | 1939198 A1 | 7/2008 |
| EP | 1970373 A1 | 9/2008 |
| EP | 2133353 A1 | 12/2009 |
| EP | 2138497 A1 | 12/2009 |
| JP | 64063582 | 3/1989 |
| JP | 2000053653 | 2/2000 |
| JP | 2000053654 | 2/2000 |
| JP | 2008222557 A | 9/2008 |
| JP | 2009528989 A | 8/2009 |
| JP | 4342007 A2 | 10/2009 |
| JP | 2010522151 A | 7/2010 |
| WO | 199801448 A1 | 1/1998 |
| WO | 199808847 A1 | 3/1998 |
| WO | 199814448 A1 | 4/1998 |
| WO | 199850370 A1 | 11/1998 |
| WO | 199928321 A1 | 6/1999 |
| WO | 199932122 A1 | 7/1999 |
| WO | 199940091 A1 | 8/1999 |
| WO | 199941253 A1 | 8/1999 |
| WO | 200006577 A1 | 2/2000 |
| WO | 2000061562 A1 | 10/2000 |
| WO | 2002087513 A2 | 11/2002 |
| WO | 2002088080 A2 | 11/2002 |
| WO | 2003055890 A1 | 7/2003 |
| WO | 2004029054 A1 | 8/2004 |
| WO | 2005007672 A2 | 1/2005 |
| WO | 2005092892 A1 | 10/2005 |
| WO | 2005092893 A1 | 10/2005 |
| WO | 2006015985 A1 | 2/2006 |
| WO | 2006050843 A1 | 5/2006 |
| WO | 2006117670 A1 | 11/2006 |
| WO | 2006120252 A2 | 11/2006 |
| WO | 2007034881 A1 | 3/2007 |
| WO | 2007056208 A1 | 5/2007 |
| WO | 2007063934 A1 | 6/2007 |
| WO | 2007084413 A2 | 7/2007 |
| WO | 2007093901 A1 | 8/2007 |
| WO | 2008009078 A2 | 1/2008 |
| WO | 2008073785 A2 | 6/2008 |
| WO | 2008075103 A1 | 6/2008 |
| WO | 2009032668 A2 | 8/2008 |
| WO | 2008114008 A1 | 9/2008 |
| WO | 2008114817 A1 | 9/2008 |
| WO | 2008114819 A1 | 9/2008 |
| WO | 2008115319 A2 | 9/2008 |
| WO | 2008147697 A1 | 12/2008 |
| WO | 2009005687 A1 | 1/2009 |
| WO | 2009023179 A2 | 2/2009 |
| WO | 2009030998 A1 | 3/2009 |
| WO | 2009067081 A1 | 5/2009 |
| WO | 2009080836 A2 | 7/2009 |
| WO | 2009099650 A2 | 8/2009 |
| WO | 2009134624 A1 | 11/2009 |
| WO | 2010006025 A1 | 1/2010 |
| WO | 2010007116 A3 | 1/2010 |
| WO | 2010133885 A1 | 11/2010 |
| WO | 2011014535 A1 | 2/2011 |
| WO | 2011049825 A1 | 4/2011 |
| WO | 2011049987 | 4/2011 |
| WO | 2011062253 A1 | 5/2011 |
| WO | 2011062372 A3 | 5/2011 |
| WO | 2012066335 A1 | 5/2012 |
| WO | 2012067269 A1 | 5/2012 |
| WO | 2012136834 | 10/2012 |
| WO | 2012156498 A1 | 11/2012 |
| WO | 2013068438 A1 | 5/2013 |
| WO | 2013117615 A1 | 8/2013 |
| WO | 2014053595 A1 | 4/2014 |

OTHER PUBLICATIONS

Tran, et al, "Design and optimization of orally active TLR7 agonists for the treatment of hepatitis C virus infection". Bioorganic & Medicinal Chemistry Letters, vol. 21: pp. 2389-2393 (2011).

Ulrich, et al., "Crystallization". Kirk-othmer Encyclopedia of Chemical Technology, Chapter 4: pp. 1-63, (Aug. 16 2002).

Vedantham, et al., "Mechanism of Interferon Action in Hairy Cell Leukemia: A Model of Effective Cancer Biotherapy", Cancer Research, vol. 52: pp. 1056-1066 (Mar. 1, 1992).

Warshakoon, et al., "Potential Adjuvantic Properties of Innate Immune Stimuli", Human Vaccines, vol. 5(6): pp. 381-394 (Jun. 2009).

Wermuth, "Molecular Variations Based on Isosteric Replacements", The Practice of Medicinal Chemistry, 1996, pp. 203-237, Ch. 13.

Wolff, et al., Burger's Medicinal Chemistry and Drug Discovery,-, 1994, pp. 975-977, 5th Edition, vol. 1.

Yu, et al., "Toll-Like Receptor 7 Agonists: Chemical Feature Based", PLOS One, vol. 8 (3): pp. 1-11 e56514, (Mar. 20, 2013).

Yu, et al., "Dual Character of Toll-Like Receptor Signaling: Pro-Tumorigenic Effects and Anti-Tumor Functions", Biochimica et Biophysica Acta, vol. 1835: pp. 144-154 (2013).

Zhao, et al., Toll-Like Receptors and Prostate Cancer . Frontiers in Immunology, vol. 5 (Article 352): pp. 1-7 (Jul. 2014).

Wan, et al., Organic Letters, 2006, 8(11), 2425-2428.

Isobe, et al., "Synthesis and Biological Evaluation of Novel 9-Substituted-8-Hydroxyadenine Derivatives as Potent Inferferon Inducers", J. Med. Chem., vol. 49; pp. 2088-2095 (2006).

Jurk, et al., "Human TLR7 or TLR8 Independently Confer Responsiveness to the Antiviral Compound R-848", Nature Immunology, Jun. 2002, pp. 499, vol. 3 (6).

Kurimoto, et al., "Synthesis and Evaluation of 2-Substituted 8-Hydroxyadenines as Potent Interferon Inducers with Improved Oral Bioavailabilities", Bioorganic & Medicinal Chemistry, vol. 12; pp. 1091-1099 (2004).

Lee, et al., "Activation of Anti-Hepatitis C Virus Responses via Toll-Like Receptor 7", PNAS, vol. 3 (6); pp. 1828-1833 (Feb. 7, 2006).

Roethle, et al., "Identification and Optimization of Pteridinone Toll-Like Receptor 7 (TLR7) Agonists for the Oral Treatment of Viral Hepatitis", Journal of Medicinal Chemistry, vol. 56; pp. 7324-73333 (2013).

R. J. Ulevitch, "Therapeutics Targeting the Innate immune System", Nature, vol. 4: pp. 512-520 (Jul. 2004).

Horscroft, et al, "Antiviral applications of toll-like receptor agonists", J. Antimicrob. Chemother., pp. 1-13 (Jan. 18, 2016).

J. A. Hoffmann, "The Immune Response of *Drosophila*", Nature, vol. 426: pp. 33-38 (2003).

Makkouk et al., "The potential use of Toll-Like Receptors (TLR) agonistd and antagonists as prophylactic and/or therapeutic agents", Immunopharmacology and Immunotoxicology, vol. 31(3): pp. 331-338 (2009).

O'Hara, et al., "Regioselective Synthesis of Imidazo[4,5-g]quinazoline Quinone Nucleosides and Quinazoline mino Nucleosides. Studies of their Xanthine Oxidase and Purine Nucleoside Phosphorylase Substrate Activity", J. Org. Chem. vol. 56., pp. 776-785 (1991).

Takeda, et al., Toll-Like Receptors, Annu. Rev. Immunol, 2003, pp. 335-376, vol. 21.

Thomas, et al., "Investigating Toll-Like Receptor Agonists for Potential To Treat Hepatitis C Virus Infection", Antimicrobial Agents and Chemotherapy, vol. 51(8): pp. 2969-2978 (Aug. 2007).

(56) References Cited

OTHER PUBLICATIONS

Vippagunta, et al., "Crystalline Solids", Advance Drug Delivery Reviews, vol. 48: pp. 3-26 (2001).
Yin, et al., "Synthesis of 2,4-Diaminoquinazolines and Tricyclic Quinazolines by Cascade Reductive Cyclization of Methyl N-Cyano-2-nitrobenzimidates", J. Org. Chem., vol. 77: pp. 2649-2658 (2012).
Banker (Editor), "Prodrugs", Modem Pharmaceutics, Third Edition: pp. 596 (1976).
Baraldi, et al., "New Strategies for the Synthesis of A3 Adenosine Receptor Antagonists", Bioorganic & Medicinal Chemistry, vol. 11: pp. 4161-4169 (2003).
Barker, et al., "A Rapid Conversion of 3-0xothiolanes into 3-Aminothiophenes", Synthetic Communications, vol. 32(16): pp. 2565-2568 (2002).
Bell, et al., "Chemistry of 5-Pyrimidinecarboxaldehydes", Journal of Heterocyclic Chemistry, vol. 29: pp. 41-44 (Jan.-Feb. 1983).
Bennet, et al. (Editor), "Part XIV Oncology", Cecil Textbook of Medicine. vol. 1, 20th Edition: pp. 1004-1010 (1996).
Bizanek, et al., Isolation and Structure of an Intrastrand Cross-Link Adduct of Mitomycin C nd DNA, Biochemistry, 1992, pp. 3084-3091, vol. 31.
Brittain, et al., "Effects of Pharmaceutical Processing on Drug Polymorphs and Solvates", Polymorphism in Pharmaceutical Solids, 1999, pp. 331-360, Chapter 8.
Organic Syntheses Collective, "3-Methylcoumarone", Organic Syntheses Collective, 1963, pp. 43-46, vol. 4.
Bruns, et al, "Solubilities of Adenosine Antagonists Determined by Radioreceptor Assay", Journal of Pharmacy and Pharmacology, vol. 41: pp. 590-594 (1989).
Chawla, et al., "Challenges in Polymorphism of Pharmaceuticals", Current Research & Information on Pharmaceutical Sciences, vol. 5(1): pp. 9-12 (Jan.-Mar. 2004).
Abdillahi, et al., "Synthesis of a Novel Series of Thieno[3,2-d]pyrimidin-4-{3H)-ones", Synthesis, vol. 9: pp. 1428-1430 (2010).
De Clercq, et al., "(S)-9-(2,3-Dihydroxypropyl)adenine: An Aliphatic Nucleoside Analaog with Broad-Spectrum Antiviral Activity", Science, 1978, pp. 563-565, vol. 200.
De Nardo, "Toll-Like Receptors: Activation, Signalling and Transcriptional Modulation", Cytokine, 2015, pp. 181-189, vol. 74.
Dermer. "Another Anniversary for the War on Cancer", Bio/Technology, vol. 12: pp. 320 (Mar. 1994).
Douglas, Jr, Introduction of Viral Diseases•, Cecil Textbook of Medicine, 2Dth Edition, vol. 2: pp. 1973-42 (1996).
Freshney, et al., Culture of Animal Cells, Manual of Basic Technique, 1983, pp. 1-6, Chapter 1.
Fried, et al., Peginterferon Alfa-2a Plus Ribavirin for Chronic Hepatitis C Virus Infection-, New England Journal of Medicine, Sep. 26, 2002, pp. 975-985, vol. 347 (13).
Grimm, et al., "Toll-like receptor (TLR) 7 and TLR8 expression on CD133+ cells in colorectal cancer points to a specific rold for inflammation inducted TLRs in tumourigenesis and tumour progression", European Journal of Cancer, 2010, pp. 2849-2857, vol. 46.
Hackam, et al, Translation of Research Evidence From animals to Humans-. JAMA, vol. 296 (14): pp. 1731-1732 (2006).
Hood, et al.,-"Immunoprofiling toll-like receptor ligands Comparison of Immunostimulatory and proinflammatory profiles in ex vivo human blood models", Human Vaccines, vol. 6(4): pp. 322-335 (Apr. 2010).
Huddleston, et al., "A Convenient Synthesis of 2-Substituted 3-Hydroxy-And 3-Amino-Thiophens From Derivatives of 2-Choroacrylic Acid", Synthetic Communications, vol. 9(8): pp. 731-734 (1979).
Jiang, et al., "Synthesis of 4-chlorothieno[3,2-d]pyrimidine", Chemical Industry and Engineering Progress, vol. 30: pp. 2532-2535, (2011). [With English Abstract].
Jordan, "Tamoxifen: A Most Unlikely Pioneering Medicine", Nature Reviews, vol. 2: pp. 205-213, (Mar. 2003).
Kanzler, et al., "Therapeutic Targeting of Innate Immunity with Toll-Like Receptor Agonists and Antagonists", Nature Medicine, vol. 13(5): pp. 552-559 (May 2007).
Krieger, et al, Enhancement of Hepatitis C Virus RNA Replication by Cell Culture, Journal of Virology, May 1, 2001, 4614-1624, 75-10, DE.
Kurimoto, et al., "Synthesis and Structure-Activity Relationships of 2-Amino-B-hydroxyadenines as Orally Active Interferon Inducing Agents", Bioorganic & Medicinal Chemistry, vol. 11: pp. 5501-5508 (2003).
Liu, et al., "Synthesis and Biological Activity of 3-and 5-Amino Derivatives of Pyridine-2Carboxaldehyde Thiosemicarbazone", J. Med. Chem, Vo. 39: pp. 2586-2593 (1996).
Lohmann et al, Viral and Cellular Determinants of Hepatitis C Virus RNA Replication in Cell Culture, Journal of Virology, Mar. 2003, pp. 3007-3019, vol. 77, No. 5.
Lohmann, et al., Replication of Subgenomic Hepatitis C Virus RNAs in a Hepatoma Cell Line, Science, 1999, pp. 110-113, vol. 285.
McGowan et al., "Novel Pyrimidine Toll-Like Receptor 7 and 8 Dual Agonists to Treat Hepatitis B Virus", Journal of Medicinal Chemistry, 2016, pp. 7936-7949, vol. 59 No. 17.
Mesguiche, et al., "4-Alkoxy-2,6-diaminopyrimidine Derivatives: Inhibitors of Cyclin Dependent Kinases 1 and 2", Bioorganic & Medicinal Chemistry Letters, vol. 13: pp. 217-222 (2003).
Moreau, et al., "Synthesis of cyclic adenosine 5'-diphosphate ribose analogues: a C2' endo/syn "southern" ribose conformation underlies activity at the sea urchin cADPR receptor", Organic & Biomolecular Chemistry, vol. 9: pp. 278-290 (2011).
Musmuca, et al, "Small-Molecule interferon Inducers. Toward the Comprehension of the Molecular Determinants through Ligand-Based Approaches", J. Chem. Inf. Model., vol. 49: pp. 1777-1786 (2009).
Newman, et al., "Solid-State Analysis of the Active Pharmaceutical Ingredient in Drug Products", Drug Discovery Today, Oct. 19, 2003, pp. 898-905, vol. 8(19).
Ohto, et al., "Structure and Function of Toll-Like Receptor 8", Microbes and Infections, vol. 16: pp. 273-282 (2014).
U.S. Appl. No. 14/118,527, filed Nov. 18, 2013, David McGowan.
U.S. Appl. No. 14/443,305, filed May 15, 2015, Stefaan Julien Last.
U.S. Appl. No. 15/591,473, filed May 10, 2017, Stefaan Julien Last.
U.S. Appl. No. 16/377,752, filed Apr. 8, 2019, Stefaan Julien Last.

HETEROCYCLIC SUBSTITUTED 2-AMINO QUINAZOLINE DERIVATIVES FOR THE TREATMENT OF VIRAL INFECTIONS

CROSS-REFERENCE TO RELATED APPLICATIONS

This application is a continuation of U.S. patent application Ser. No. 15/591,473, filed on May 10, 2017, which is a continuation of U.S. patent application Ser. No. 14/443,305, filed on May 15, 2015, now U.S. Pat. No. 9,663,474, which is a national phase entry of International Application No. PCT/EP2013/073901 filed Nov. 15, 2013, which claims priority to European patent application EP 12192970.7 filed Nov. 16, 2012, each of which are incorporated herein in its entirety.

SEQUENCE LISTING

The instant application contains a Sequence Listing which has been submitted electronically in ASCII format and is hereby incorporated by reference in its entirety. This ASCII copy, created on Apr. 4, 2019, is named TIP0289USCNT2_SL.txt and is 657 bytes in size.

This invention relates to heterocyclic substituted 2-amino-quinazoline derivatives, processes for their preparation, pharmaceutical compositions, and their use in treating viral infections.

The present invention relates to the use of heterocyclic substituted 2-amino-quinazoline derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

It has been estimated that most mammalian species have between ten and fifteen types of Toll-like receptors. Thirteen TLRs (named TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For reviews on TLRs see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as purine derivatives in WO 2006/117670, adenine derivatives in WO 98/01448 and WO 99/28321, and pyrimidines in WO 2009/067081.

However, there exists a strong need for novel Toll-Like receptor modulators having preferred selectivity, higher potency, higher metabolic stability, and an improved safety profile compared to the compounds of the prior art.

In accordance with the present invention a compound of formula (I) is provided

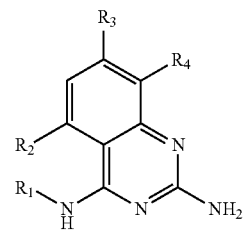

or a pharmaceutically acceptable salt, tautomer(s), stereoisomeric forms, solvate or polymorph thereof, wherein
$R_1$ is any of the following structures

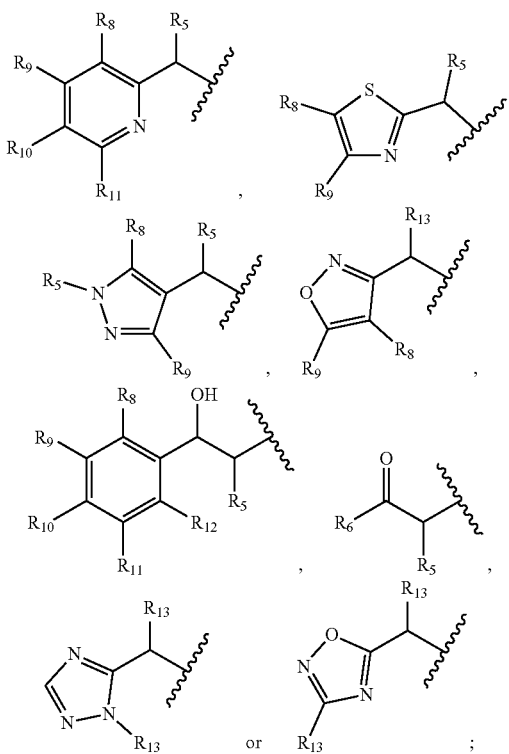

$R_2$ is hydrogen, —O—$(C_{1-3})$-alkyl, halogen, $(C_{1-3})$-alkyl, —O—$(C_{1-3})$-alkyl-O—$(C_{1-3})$-alkyl or $CH_2OH$;

$R_3$ is hydrogen, —O—$(C_{1-3})$-alkyl, halogen, $(C_{1-3})$-alkyl or —C(=O)—$R_7$ wherein $R_7$ is —O—$(C_{1-3})$-alkyl, $NH_2$, $NH(CH_3)$, $N(CH_3)_2$, $N(CH_3)(C_{1-3})$-alkyl, $N((C_{1-3})$-alkyl$)_2$ or pyrrolidine;

$R_4$ is hydrogen or fluorine;

$R_5$ is $(C_{1-3})$-alkyl, $(C_{1-3})$-fluoro-alkyl or $CH_2OH$;

$R_6$ is $NH_2$, $NH(CH_3)$ or $N(CH_3)_2$, (hetero)-anilines optionally substituted with one or more $R_8$, $R_9$, $R_{10}$ $R_{11}$ or $R_{12}$ or (hetero)-benzylamines optionally substituted with one or more $R_8$, $R_9$, $R_{10}$ $R_{11}$ or $R_{12}$, $R_8$, $R_9$, $R_{10}$, $R_{11}$ and $R_{12}$ which are the same or different, are each independently selected from hydrogen, $(C_{1-3})$-alkyl, —O—$(C_{1-3})$-alkyl or halogen
and
$R_{13}$ is hydrogen, $(C_{1-3})$-alkyl or $(C_{1-3})$-fluoro-alkyl.

Preferred compounds according to the invention are compounds with the numbers 12 and 29 as depicted in Table II.

The compounds of formula (I) and their pharmaceutically acceptable salts, tautomer(s), stereo-isomeric forms, solvate or polymorph thereof have activity as pharmaceuticals, in particular as modulators of Toll-Like Receptors (especially TLR7 and/or TLR8 activity).

In a further aspect the present invention provides a pharmaceutical composition comprising a compound of formula (I) or a pharmaceutically acceptable salt, tautomer, stereo-isomeric form, solvate or polymorph thereof together with one or more pharmaceutically acceptable excipients, diluents or carriers.

Furthermore a compound of formula (I) or a pharmaceutically acceptable salt, solvate, tautomer, stereo-isomeric form or polymorph thereof according to the current invention, or a pharmaceutical composition comprising said compound of formula (I) or a pharmaceutically acceptable salt, solvate, tautomer, stereo-isomeric form or polymorph thereof can be used as a medicament.

Another aspect of the invention is that a compound of formula (I) or its pharmaceutically acceptable salt, solvate, tautomer, stereo-isomeric form or polymorph thereof, or said pharmaceutical composition comprising said compound of formula (I) or a pharmaceutically acceptable salt, solvate, tautomer, stereo-isomeric form or polymorph thereof can be used accordingly in the treatment of a disorder in which the modulation of TLR7 and/or TLR8 is involved.

The term "$(C_{1-3})$-alkyl" refers to a straight-chain, branched-chain or cyclic saturated aliphatic hydrocarbon containing the specified number of carbon atoms.

The term "$(C_{1-3})$-fluoro-alkyl" refers to a straight-chain, branched-chain or cyclic saturated aliphatic hydrocarbon containing the specified number of carbon atoms where one or more hydrogen atoms was replaced by a fluorine atom.

The term "halogen" refers to fluorine, chlorine, bromine or iodine, preferably to fluorine and chlorine.

The term "aniline" refers a compound with the formula $C_6H_5NR_{13}$— consisting of a phenyl group attached to an amino group; with "(hetero)-aniline" is meant that in the aromatic ring 1-3 nitrogen atoms, preferably 1 nitrogen atom, are present.

The term "benzylamine" means a compound of the formula $C_6H_5CH_2NR_{13}$— consisting of a benzyl group, $C_6H_5CH_2$, attached to an amine functional group; with "(hetero)-benzylamine" is meant that in the aromatic ring 1-3 nitrogen atoms, preferably 1 nitrogen atom, are present.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration. If a compound contains an at least disubstituted non-aromatic cyclic group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S.

Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

Preparation of Compounds of Formula (I)

Compounds of formula (I) are prepared according to scheme 1. Substituted anthranilic esters or acids (II) were heated under acidic conditions in the presence of excess cyanamide, using an alcoholic solvent (e.g. ethanol) or diglyme according to the method described in the literature (O'Hara et. al. JOC (1991) 56, p 776). Subsequent amine substitution of the 2-amino-4-hydroxyquinazolines (III) can proceed via a coupling agent such as BOP or PyBOP in the presence of DBU and the amine in a polar aprotic solvent (e.g. DMF).

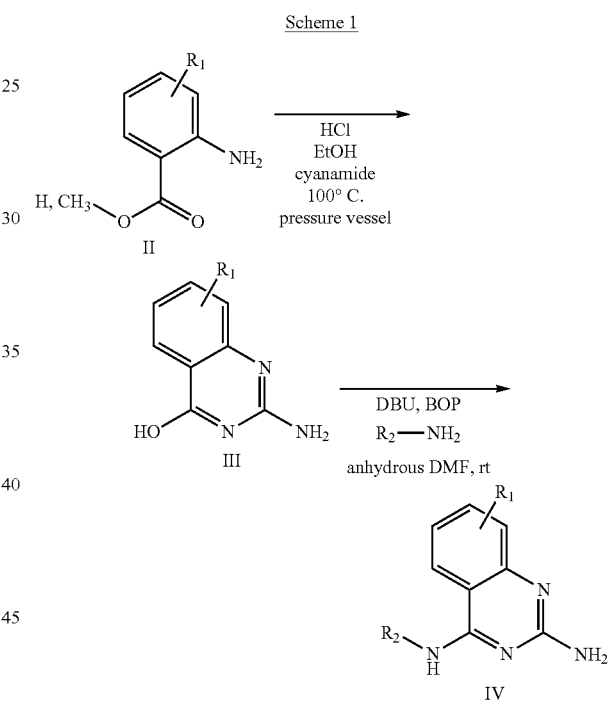

Scheme 1

EXPERIMENTAL SECTION

General Procedure of Making a Substituted 2-amino-4-hydroxyquinazoline

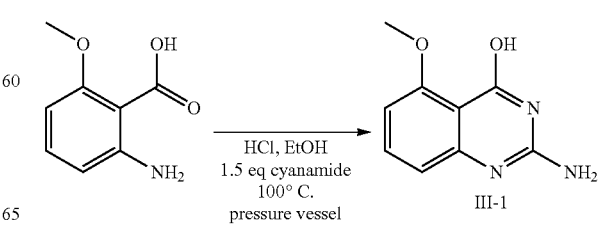

Into a 500 mL pressure vessel equipped with a magnetic stir bar was placed 2-amino-6-methoxybenzoic acid (25 g, 149.6 mmol), ethanol (200 mL), cyanamide (9.43 g, 224 mmol), and concentrated HCl (6 mL). The mixture was allowed to stir at 100° C. for 16 h. The reaction mixture was allowed to cool to room temperature and the solids were isolated via filtration and washed with ethanol and DIPE. The crude product was dried under vacuum at 50° C. to obtain an off white solid.

LC-MS m/z=192(M+H)

$^1$H NMR (400 MHz, DMSO-d$_6$) δ ppm 3.88 (s, 3H), 6.96 (dd, J=8.2, 3.1 Hz, 2H), 7.69 (t, J=8.3 Hz, 1H), 8.28 (br. s., 2H), 12.67 (br. s., 1H)

TABLE I

Compounds of formula (III). The following intermediates were prepared according to the method to prepare III-1.

| # | STRUCTURE | H NMR | LCMS (M+H)$^+$ |
|---|---|---|---|
| 1 | 5-fluoro-4-hydroxy-2-aminoquinazoline | $^1$H NMR (400 MHz, DMSO-d$_6$) δ ppm 6.98 (dd, J = 11.0, 8.3 Hz, 1 H), 7.13 (d, J = 8.3 Hz, 1 H), 7.51 (br. s., 2 H), 7.64 (td, J = 8.3, 5.8 Hz, 1 H), 12.30 (br. s, 1 H) | 180 |
| 2 | 7-fluoro-4-hydroxy-2-aminoquinazoline | $^1$H NMR (400 MHz, DMSO-d$_6$) δ ppm 7.01-7.16 (m, 2 H), 7.56 (br. s., 2 H) 7.99 (t, J = 7.7 Hz, 1 H), 10.38-13.48 (m, 1 H) | 180 |
| 3 | 8-fluoro-4-hydroxy-2-aminoquinazoline | $^1$H NMR (400 MHz, DMSO-d$_6$) δ ppm 6.51-6.67 (m, 2 H), 7.00-7.08(m, 1 H), 7.42(ddd, J = 11.2, 7.9 1.3 Hz, 1 H), 7.69 (dd, J = 7.9, 0.6 Hz, 1 H), 11.08 (br. s., 1 H) | 180 |
| 4 | 7-methyl-4-hydroxy-2-aminoquinazoline | $^1$H NMR (400 MHz, DMSO-d$_6$) δ ppm 2.43 (s, 3 H), 7.22 (d, J = 1.0 Hz, 1 H), 7.24 (s, 1 H), 7.89 (d, J = 8.0 Hz, 1 H), 8.29 (br. s., 2 H), 12.65 (br. s, 1 H) | 176 |
| 5 | 7-methoxy-4-hydroxy-2-aminoquinazoline | Not available | 192 |
| 6 | 7-chloro-4-hydroxy-2-aminoquinazoline | $^1$H NMR (400 MHz, DMSO-d$_6$) δ ppm 7.41 (dd, J = 8.5, 2.0 Hz, 1 H), 7.55 (d, J = 2.0 Hz, 1 H), 7.98 (d, J = 8.5 Hz, 1 H), 8.49 (br. s., 2 H), 10.79-13.69 (m, 1 H) | 196 |
| 7 | methyl 4-hydroxy-2-aminoquinazoline-7-carboxylate | $^1$H NMR (400 MHz, DMSO-d$_6$) δ ppm 3.87-3.95 (m, 3 H), 7.12-7.47 (m, 1 H), 7.83 (dd, J = 8.3, 1.4 Hz, 1 H), 7.99 (d, J = 1.3 Hz, 1 H), 8.07-8.13 (m, 1 H), 8.43 (br. s., 2 H) | 220 |

TABLE I-continued

Compounds of formula (III). The following intermediates were prepared according to the method to prepare III-1.

| # | STRUCTURE | H NMR | LCMS (M+H)+ |
|---|---|---|---|
| 8 | 5-methyl-2-amino-quinazolin-4-ol | Not available | 174 (M-H)− |
| 9 | 5-methoxy-2-amino-quinazolin-4-ol | $^1$H NMR (400 MHz, DMSO-$d_6$) δ ppm 3.74-3.82 (m, 3 H), 6.42 (br. s., 2 H), 6.62 (d, J = 7.7 Hz, 1 H), 6.75 (dd, J = 8.3, 0.8 Hz, 1 H), 7.44 (t, J = 8.3 Hz, 1 H), 10.91 (br. s., 1 H) | 192 |
| 10 | 5-bromo-8-fluoro-2-amino-quinazolin-4-ol | $^1$H NMR (400 MHz, DMSO-$d_6$) δ ppm 7.40 (dd, J = 8.7, 4.7 Hz, 1 H), 7.48 (t, J = 8.8 Hz, 1 H) | NA |

General Procedure of Making Compound IV

Compound III (1.5 mmol) and DBU (3.75 mmol) were dissolved in 5 mL DMF in a 30 mL glass vial. After 5 minutes BOP (1.5 mmol) was added. The reaction mixture was stirred for 5 minutes and then the amine (2.25 mmol) was added. The reaction mixture was stirred overnight. The crude reaction mixture was purified by prep. HPLC on (RP Vydac Denali C18—10 μm, 250 g, 5 cm). Mobile phase (0.25% NH$_4$HCO$_3$ solution in water, MeOH), the desired fractions were collected, evaporated, dissolved in MeOH and evaporated again to obtain the product as a solid.

General Procedure to Make Compounds 22, 23, 24, 26, 27 and 28

Compound 8 of formula (I) (see table II) (2.1 g, 6.5 mmol) was dispensed in THF (50 mL), LiOH (409 mg, 9.74 mmol) was added followed by MeOH (5 mL). The reaction mixture was stirred overnight at room temperature. The solvents were evaporated until only water remained. 10 mL 1M HCl was added and the compound was extracted with 2-methyltetrahydrofuran (2×25 mL). The combined organic layers were dried on MgSO$_4$ and the solvents were removed under reduced pressure to obtain 2-amino-4-[1-(2-pyridyl)ethylamino]quinazoline-7-carboxylic acid as a white solid.

2-amino-4-[1-(2-pyridyl)ethylamino]quinazoline-7-carboxylic acid (200 mg, 0.65 mmol) and PyBOP (421 mg, 0.81 mmol) were dissolved in DMF (5 mL) in a 30 mL glass vial. After 5 minutes Hunig's base (0.557 mL, 3.23 mmol) was added. The reaction mixture was stirred for 5 minutes and then the amine was added. The reaction mixture was stirred overnight. The crude reaction mixture was purified by preparative. HPLC on (RP Vydac Denali C18—10 μm, 250 g, 5 cm). Mobile phase (0.25% NH$_4$HCO$_3$ solution in water, MeOH), the desired fractions were collected, evaporated, dissolved in MeOH and evaporated again to obtain the product as a solid.

Procedure to Make Compound 29

Compound 12 of formula (I) (see table II) (1500 mg, 4.78 mmol) and pyridine hydrochloride (3.32 g, 28.7 mmol) were dissolved in pyridine (20 mL) and heated to 120° C. for 16 h. Pyridine was removed under reduced pressure. The residual fraction was quenched with a NaHCO$_3$ (sat., aq.) solution. The precipitate was filtered off, washed with water and dried under vacuum at 50° C. to afford a brown solid which was purified by preparative HPLC (Stationary phase: RP Vydac Denali C18—10 μm, 200 g, 5 cm), Mobile phase: 0.25% NH$_4$HCO$_3$ solution in water, CH$_3$CN), the desired fractions were collected, evaporated, dissolved in MeOH and evaporated again to obtain 2-amino-4-[(5-methylisoxazol-3-yl)methylamino]quinazolin-5-ol (100 mg) as a solid.

2-amino-4-[(5-methylisoxazol-3-yl)methylamino]quinazolin-5-ol (40 mg, 0.15 mmol) and Cs$_2$CO$_3$ (144 mg, 0.44 mmol) were dissolved in DMF (7.5 mL) and stirred at room temperature for 30 minutes. 2-bromoethyl methyl ether (0.018 mL, 0.18 mmol) was added and the entire mixture was stirred for 16 hours at room temperature. The solvent was removed under reduced pressure and the crude residue was neutralized with 1M HCl and purified by preparative HPLC on (RP Vydac Denali C18—10 μm, 250 g, 5 cm). Mobile phase (0.25% NH$_4$HCO$_3$ solution in water, MeOH), the desired fractions were collected, evaporated, dissolved in MeOH and evaporated again to obtain compound 29 as a solid.

Procedure to Make Compound 30

A 75-mL stainless steel autoclave was charged under N$_2$ atmosphere with 2-amino-5-bromo-quinazolin-4-ol (3 g, 12.5 mmol), Pd(OAc)$_2$ (56 mg, 0.25 mmol), 1,3 bis(diphenylphosphino)propane (206 mg, 0.5 mmol), potassium acetate (2.45 g, 25 mmol), methanol (25 mL) and THF (30 mL). The autoclave was closed and pressurized to 50 bar CO gas and the reaction was carried out for 16 hours at 100° C. The formed precipitate was removed by filtration yielding methyl 2-amino-4-hydroxy-quinazoline-5-carboxylate (2.35 g).

Methyl 2-amino-4-hydroxy-quinazoline-5-carboxylate (2.35 g) in THF (10 mL) was cooled to 0° C. Then LiAlH$_4$ was added. The mixture was allowed to reach room temperature and stirred for 16 hours. EtOAc (5 mL) was added drop wise at 0° C., then 3 g Na$_2$SO$_4$.10H$_2$O was added and the entire mixture was stirred for 30 minutes. The precipitate was filtered off, and the filtrate was dried with MgSO$_4$, filtered and evaporated to dryness to obtain 2-amino-5-(hydroxymethyl)quinazolin-4-ol (750 mg) as a yellow solid.

2-amino-5-(hydroxymethyl)quinazolin-4-ol (300 mg, 1.57 mmol) was suspended in THF (20 mL) with DBU (0.586 mL, 3.92 mmol), after 5 minutes BOP (833 mg, 1.88 mmol) was added. After 15 minutes (5-methyl-3-isoxazolyl)methylamine (0.320 mL, 3.14 mmol) was added. The mixture was stirred for 16 hours at room temperature. The solvent was removed under reduced pressure and the crude product was purified by preparative HPLC on (RP Vydac Denali C18—10 μm, 250 g, 5 cm). Mobile phase (0.25% NH$_4$HCO$_3$ solution in water, MeOH), the desired fractions were collected, evaporated, dissolved in MeOH and evaporated again to obtain compound 30 as a solid (119 mg).

Procedure to Make Compound 31

A freshly prepared NaOMe solution (1.25 mL, 6.25 mmol) was added under N$_2$ atmosphere to a mixture of 2-amino-5-bromo-8-fluoro-quinazolin-4-ol (500 mg, 1.94 mmol), copper (I) bromide (39 mg, 0.27 mmol), EtOAc (0.076 mL, 0.78 mmol) in MeOH (5 mL). The mixture was heated up in a pressure vessel to reflux for 16 hours. The solvent was removed under reduced pressure. The residue was purified by preparative HPLC (Stationary phase: RP Vydac Denali C18—10 μm, 200 g, 5 cm), Mobile phase: 0.25% NH$_4$HCO$_3$ solution in water, MeOH), the desired fractions were collected, evaporated, dissolved in MeOH and evaporated again to obtain 2-amino-8-fluoro-5-methoxy-quinazolin-4-ol (150 mg) as a solid.

2-amino-8-fluoro-5-methoxy-quinazolin-4-ol (150 mg, 0.72 mmol) was dispensed in DMF (10 mL), DBU (0.536 mL, 3.59 mmol), was added and then BOP reagent (396 mg, 0.90 mmol) was added. The reaction mixture was stirred and when it was homogeneous (5-methyl-3-isoxazolyl)methylamine (0.115 mL, 1.08 mmol) was added. The reaction mixture was stirred 16 hours. The reaction was concentrated under reduced pressure and the residue was purified by preparative HPLC (Stationary phase: RP Vydac Denali C18—10 μm, 200 g, 5 cm), Mobile phase: 0.25% NH$_4$HCO$_3$ solution in water, MeOH), the desired fractions were collected, evaporated, dissolved in MeOH and evaporated again to obtain compound 31 as a solid (64 mg).

Procedure to Make Compound 32

Compound 31 (52.5 mg, 0.173 mmol) and pyridine hydrochloride (0.12 g, 1.039 mmol) in 1 mL pyridine was heated to 120° C. for 16 hours. The volatiles were removed under reduced pressure. The residue was quenched with a NaHCO$_3$ (sat., aq.) solution. The precipitate was filtered off, washed with water and dried under vacuum at 50° C. to afford 2-amino-8-fluoro-4-[(5-methylisoxazol-3-yl)methylamino]quinazolin-5-ol (10 mg) as a brown solid.

2-amino-8-fluoro-4-[(5-methylisoxazol-3-yl)methylamino]quinazolin-5-ol (10 mg, 0.035 mmol) and Cs$_2$CO$_3$ (33.8 mg, 0.104 mmol) in DMF (5 mL) was stirred at room temperature for 30 minutes. 2-chloroethyl methyl ether (4.1 mg, 0.043 mmol) was added and the entire mixture was stirred for 16 hours at room temperature. The solvent was removed under reduced pressure. The residue was dissolved in MeOH and the precipitate (salts) were removed by filtration. The filtrate was concentrated under reduced pressure and the crude residue was purified by preparative HPLC on (Stationary phase: RP SunFire Prep C18 OBD-10 μm, 30×150 mm), Mobile phase: 0.25% NH$_4$HCO$_3$ solution in water, CH$_3$CN), the desired fractions were collected, evaporated, dissolved in MeOH and evaporated again to obtain compound 32 as a solid (2 mg).

TABLE II

Compounds of formula (I). The following compounds were synthesized according to one of the methods described above.

| # | STRUCTURE | H NMR |
|---|-----------|-------|
| 1 | 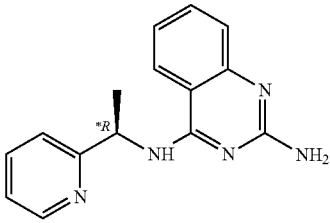 [SMILES: C[C@@H](Nc1nc(N)nc2ccccc12)c1ccccn1] | $^1$H NMR (400 MHz, DMSO-d$_6$) δ ppm 1.60 (d, J = 7.3 Hz, 3 H), 5.61 (quin, J = 7.3 Hz, 1 H), 5.97 (s, 2 H), 7.05 (ddd, J = 8.1, 6.9, 1.2 Hz, 1 H), 7.20 (dd, J = 8.4, 0.7 Hz, 1 H), 7.24 (ddd, J = 7.5, 4.8, 0.9 Hz, 1 H), 7.44 (d, J = 7.9 Hz, 1 H), 7.49 (ddd, J = 8.3, 6.9, 1.3 Hz, 1 H), 7.72 (td, J = 7.7, 1.8 Hz, 1 H), 8.05 (d, J = 7.9 Hz, 1 H), 8.18 (dd, J = 8.3, 1.0 Hz, 1 H), 8.50-8.56 (m, 1 H) |
| 2 | 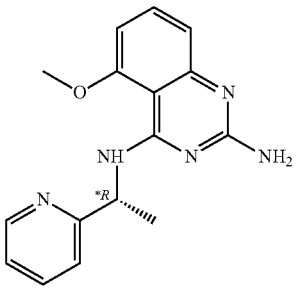 [SMILES: COc1cccc2nc(N)nc(N[C@H](C)c3ccccn3)c12] | $^1$H NMR (400 MHz, DMSO-d$_6$) δ ppm 1.53 (d, J = 6.82 Hz, 3 H) 3.99 (s, 3 H) 5.43 (t, J = 6.82 Hz, 1 H) 6.03 (s, 2 H) 6.53-6.69 (m, 1 H) 6.81 (dd, J = 8.36, 0.88 Hz, 1 H) 7.32 (ddd, J = 7.48, 4.84, 1.10 Hz, 1 H) 7.38 (t, J = 8.14 Hz, 1 H) 7.46 (d, J = 7.92 Hz, 1 H) 7.80 (td, J = 7.70, 1.76 Hz, 1 H) 8.54-8.72 (m, 1 H) 9.01 (d, J = 7.04 Hz, 1 H) |

TABLE II-continued

Compounds of formula (I). The following compounds were synthesized according to one of the methods described above.

| # | STRUCTURE | H NMR |
|---|-----------|-------|
| 3 | (structure) | ¹H NMR (400 MHz, DMSO-d₆) δ ppm 4.05 (s, 3 H), 6.25 (s, 2 H), 6.43 (quin, J = 7.8 Hz, 1 H), 6.62-6.68 (m, 1 H), 6.86 (dd, J = 8.4, 0.9 Hz, 1 H), 7.44 (t, J = 8.1 Hz, 1 H), 7.52 (ddd, J = 7.7, 4.8, 1.1 Hz, 1 H), 7.69 (d, J = 7.7 Hz, 1 H), 7.95 (td, J = 7.7, 1.8 Hz, 1 H), 8.74-8.79 (m, 1 H), 9.31 (d, J = 8.4 Hz, 1 H) |
| 4 | (structure) | ¹H NMR (400 MHz, CHLOROFORM-d) δ ppm 1.60 (d, J = 6.6 Hz, 3 H), 5.34 (br. s., 2 H), 5.49 (t, J = 6.8 Hz, 1 H), 6.78 (td, J = 8.6, 2.6 Hz, 1 H), 7.02 (dd, J = 10.8, 2.6 Hz, 1 H), 7.19 (ddd, J = 7.5, 4.8, 1.1 Hz, 1 H), 7.26-7.31 (m, 1 H), 7.59 (d, J = 6.8 Hz, 1 H), 7.65 (td, J = 7.6, 1.9 Hz, 1 H), 7.73 (dd, J = 9.0, 5.9 Hz, 1 H), 8.53-8.61 (m, 1 H) |
| 5 | (structure) | ¹H NMR (400 MHz, DMSO-d₆) δ ppm 1.58 (d, J = 7.0 Hz, 3 H), 2.35 (s, 3 H), 5.59 (quin, J = 7.3 Hz, 1 H), 5.94 (s, 2 H), 6.90 (dd, J = 8.3, 1.2 Hz, 1 H), 7.01 (s, 1 6 H), 7.23 (dd, J = 6.9, 5.2 Hz, 1 H), 7.43 (d, J = 7.9 Hz, 1 H), 7.72 (td, J = 7.7, 1.8 Hz, 1 H), 7.97 (d, J = 7.9 Hz, 1 H), 8.07 (d, J = 8.4 Hz, 1 H), 8.48-8.57 (m, 1 H) |
| 6 | (structure) | ¹H NMR (400 MHz, DMSO-d₆) δ ppm 1.57 (d, J = 7.04 Hz, 3 H) 3.80 (s, 3 H) 5.58 (t, J = 7.37 Hz, 1 H) 5.89 (s, 2 H) 6.61 (d, J = 2.42 Hz, 1 H) 6.67 (dd, J = 8.91, 2.53 Hz, 1 H) 7.23 (ddd, J = 7.48, 4.84, 0.88 Hz, 1 H) 7.42 (d, J = 7.92 Hz, 1 H) 7.72 (td, J = 7.70, 1.76 Hz, 1 H) 7.89 (d, J = 8.14 Hz, 1 H) 8.08 (d, J = 9.02 Hz, 1 H) 8.52 (dt, J = 3.96, 0.88 Hz, 1 H) |
| 7 | (structure) | ¹H NMR (400 MHz, DMSO-d₆) δ ppm 1.59 (d, J = 7.3 Hz, 3 H), 5.53-5.65 (m, 1 H), 6.21 (br. s., 2 H), 7.07 (dd, J = 8.7, 2.1 Hz, 1 H), 7.18 (d, J = 2.0 Hz, 1 H), 7.24 (ddd, J = 7.4, 4.8, 1.0 Hz, 1 H), 7.43 (d, J = 7.9 Hz, 1 H), 7.73 (td, J = 7.6, 1.9 Hz, 1 H), 8.19 (d, J = 7.9 Hz, 1 H), 8.23 (d, J = 8.8 Hz, 1 H), 8.50-8.56 (m, 1 H) |

TABLE II-continued

Compounds of formula (I). The following compounds were synthesized according to one of the methods described above.

| # | STRUCTURE | H NMR |
|---|---|---|
| 8 | 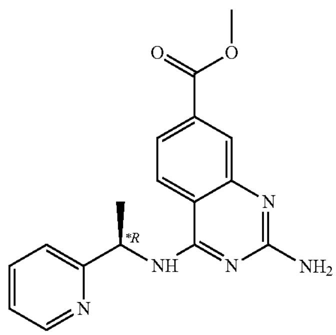 [SMILES: COC(=O)c1ccc2c(N[C@H](C)c3ccccn3)nc(N)nc2c1] | $^1$H NMR (400 MHz, DMSO-d$_6$) δ ppm 1.60 (d, J = 7.0 Hz, 3 H), 3.88 (s, 3 H), 5.61 (quin, J = 7.2 Hz, 1 H), 6.22 (s, 2 H), 7.25 (ddd, J = 7.5, 4.8, 0.9 Hz, 1 H), 7.45 (d, J = 7.9 Hz, 1 H), 7.54 (dd, J = 8.6, 1.8 Hz, 1 H), 7.70-7.77 (m, 2 H), 8.28 (d, J = 7.9 Hz, 1 H), 8.32 (d, J = 8.6 Hz, 1 H), 8.51-8.57 (m, 1 H) |
| 9 | 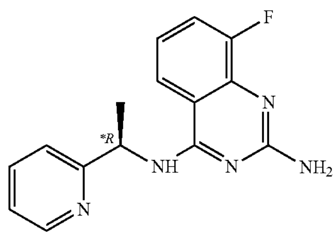 [SMILES: C[C@@H](Nc1nc(N)nc2c(F)cccc12)c1ccccn1] | $^1$H NMR (400 MHz, DMSO-d$_6$) δ ppm 1.60 (d, J = 7.04 Hz, 3 H) 5.61 (quin, J = 7.26 Hz, 1 H) 6.25 (br. s., 2 H) 6.99 (td, J = 7.98, 4.95 Hz, 1 H) 7.25 (ddd, J = 7.48, 4.84, 0.88 Hz, 1 H) 7.29-7.36 (m, 1 H) 7.44 (d, J = 7.92 Hz, 1 H) 7.73 (td, J = 7.65, 1.87 Hz, 1 H) 8.01 (d, J = 8.14 Hz, 1 H) 8.17 (d, J = 8.14 Hz, 1 H) 8.52- 8.59 (m, 1 H) |
| 10 | 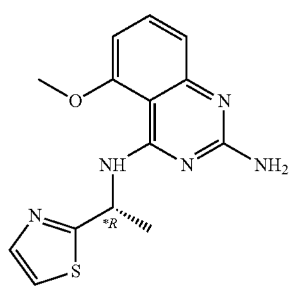 [SMILES: COc1cccc2nc(N)nc(N[C@H](C)c3nccs3)c12] | $^1$H NMR (400 MHz, DMSO-d$_6$) δ ppm 1.69 (d, J = 7.0 Hz, 3 H), 3.96 (s, 3 H), 5.80 (quin, J = 7.1 Hz, 1 H), 6.09 (s, 2 H), 6.60 (dd, J = 8.0, 0.8 Hz, 1 H), 6.83 (dd, J = 8.4, 0.9 Hz, 1 H), 7.40 (t, J = 8.3 Hz, 1 H), 7.61 (d, J = 3.1 Hz, 1 H), 7.77 (d, J = 3.3 Hz, 1 H), 8.37 (d, J = 7.7 Hz, 1 H) |
| 11 | 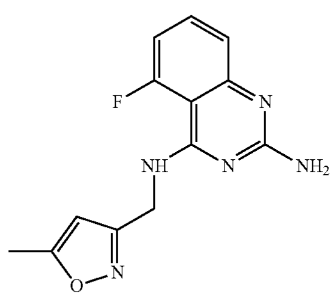 [SMILES: Cc1cc(CNc2nc(N)nc3cccc(F)c23)no1] | $^1$H NMR (400 MHz, DMSO-d$_6$) δ ppm 2.35 (d, J = 0.9 Hz, 3 H), 4.72 (d, J = 5.3 Hz, 2 H), 6.22 (d, J = 0.7 Hz, 1 H), 6.35 (s, 2 H), 6.80 (ddd, J = 12.3, 7.9, 0.9 Hz, 1 H), 7.04 (dd, J = 8.4, 0.9 Hz, 1 H), 7.46 (td, J = 8.2, 6.5 Hz, 1 H), 7.71-7.82 (m, 1 H) |
| 12 | 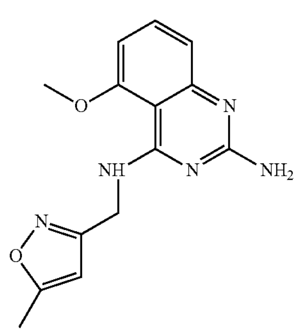 [SMILES: COc1cccc2nc(N)nc(NCc3cc(C)on3)c12] | $^1$H NMR (400 MHz, DMSO-d$_6$) δ ppm 2.36 (d, J = 0.7 Hz, 3 H), 3.92 (s, 3 H), 4.70 (d, J = 5.7 Hz, 2 H), 6.05 (s, 2 H), 6.20 (d, J = 0.7 Hz, 1 H), 6.56 (dd, J = 8.0, 0.8 Hz, 1 H), 6.81 (dd, J = 8.4, 0.9 Hz, 1 H), 7.38 (t, J = 8.1 Hz, 1 H), 8.40 (t, J = 5.8 Hz, 1 H) |

TABLE II-continued

Compounds of formula (I). The following compounds were synthesized according to one of the methods described above.

| # | STRUCTURE | H NMR |
|---|---|---|
| 13 | 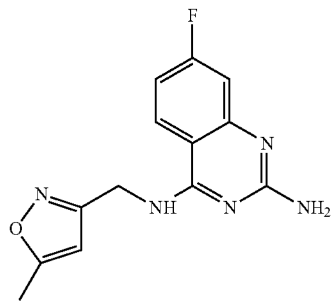 [SMILES: Cc1cc(CNc2nc(N)nc3cc(F)ccc23)no1] | ¹H NMR (400 MHz, DMSO-d₆) δ ppm 2.33-2.38 (m, 3 H), 4.67 (d, J = 5.9 Hz, 2 H), 6.18-6.24 (m, 1 H), 6.27 (s, 2 H), 6.85-6.92 (m, 2 H), 7.99-8.07 (m, 1 H), 8.42 (t, J = 5.7 Hz, 1 H) |
| 14 | 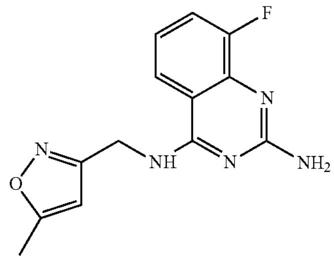 [SMILES: Cc1cc(CNc2nc(N)nc3c(F)cccc23)no1] | ¹H NMR (400 MHz, DMSO-d₆) δ ppm 2.35 (d, J = 0.9 Hz, 3 H), 4.69 (d, J = 5.9 Hz, 2 H), 6.22 (d, J = 0.9 Hz, 1 H), 6.39 (br. s., 2 H), 6.98 (td, J = 8.0, 4.8 Hz, 1 H), 7.33 (ddd, J = 11.4, 7.8, 1.1 Hz, 1 H), 7.79 (d, J = 8.4 Hz, 1 H), 8.48 (t, J = 5.8 Hz, 1 H) |
| 15 | 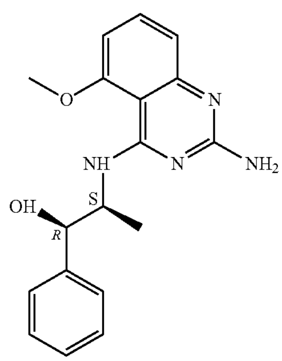 | ¹H NMR (400 MHz, DMSO-d₆) δ ppm 0.97 (d, J = 6.6 Hz, 3 H), 3.92 (s, 3 H), 4.44-4.55 (m, 1 H), 4.89 (d, J = 3.1 Hz, 1 H), 5.69 (br. s., 1 H), 6.06 (s, 2 H), 6.52-6.58 (m, 1 H), 6.79 (dd, J = 8.3, 0.8 Hz, 1 H), 7.22-7.29 (m, 1 H), 7.32-7.41 (m, 3 H), 7.43-7.49 (m, 2 H), 8.07 (d, J = 7.9 Hz, 1 H) |
| 16 | 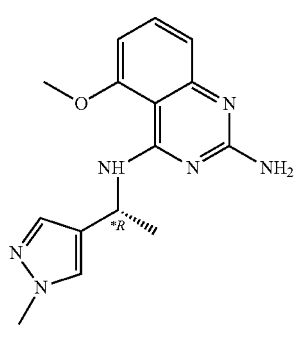 [SMILES: COc1cccc2nc(N)nc(N[C@H](C)c3cnn(C)c3)c12] | ¹H NMR (400 MHz, DMSO-d₆) δ ppm 1.51 (d, J = 6.8 Hz, 3 H), 3.79 (s, 3 H), 3.90 (s, 3 H), 5.39 (quin, J = 7.0 Hz, 1 H), 6.05 (s, 2 H), 6.52-6.58 (m, 1 H), 6.79 (dd, J = 8.4, 0.9 Hz, 1 H), 7.35 (t, J = 8.3 Hz, 1 H), 7.45 (s, 1 H), 7.68 (s, 1 H), 7.84 (d, J = 7.7 Hz, 1 H) |
| 17 | 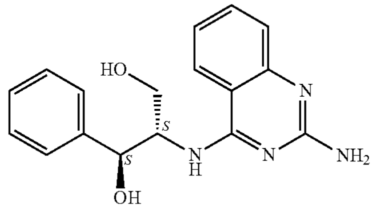 | ¹H NMR (400 MHz, DMSO-d₆) δ ppm 3.40-3.49 (m, 1 H), 3.60 - 3.71 (m, 1 H), 4.45-4.55 (m, 1 H), 4.79 (br. s., 1 H), 4.97-5.05 (m, 1 H), 5.62 (d, J = 4.8 6 Hz, 1 H), 5.98 (s, 2 H), 7.02 (t, J = 7.5 Hz, 1 H), 7.08 (d, J = 8.3 Hz, 1 H), 7.13-7.21 (m, 2 H), 7.27 (t, J = 7.5 Hz, 2 H), 7.38 (d, J = 7.3 Hz, 2 H), 7.42-7.50 (m, 1 H), 7.95 (d, J = 8.3 Hz, 1 H) |

TABLE II-continued

Compounds of formula (I). The following compounds were synthesized according to one of the methods described above.

| # | STRUCTURE | H NMR |
|---|---|---|
| 18 | 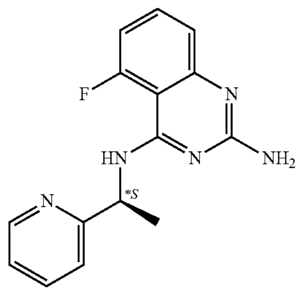 [SMILES: C[C@H](Nc1nc(N)nc2cccc(F)c12)c1ccccn1] | ¹H NMR (400 MHz, DMSO-d₆) δ ppm 1.55 (d, J = 6.82 Hz, 3 H) 5.49 (td, J = 6.77, 2.09 Hz, 1 H) 6.32 (s, 2 H) 6.82 (ddd, J = 12.76, 7.92, 0.88 Hz, 1 H) 7.05 (dd, J = 8.47, 0.99 Hz, 1 H) 7.33 (ddd, J = 7.54, 4.90, 0.99 Hz, 1 H) 7.42-7.57 (m, 2 H) 7.82 (td, J = 7.70, 1.76 Hz, 1 H) 7.93 (dd, J = 14.63, 6.93 Hz, 1 H) 8.58-8.67 (m, 1 H) |
| 19 | 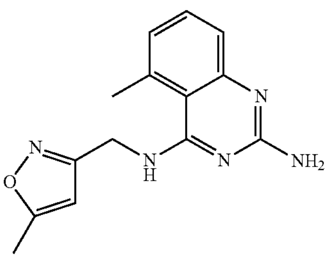 [SMILES: Cc1cc(CNc2nc(N)nc3cccc(C)c23)no1] | ¹H NMR (400 MHz, DMSO-d₆) δ ppm 2.33-2.39 (m, 3 H), 2.75 (s, 3 H), 4.71 (d, J = 5.3 Hz, 2 H), 6.06 (s, 2 H), 6.22-6.26 (m, 1 H), 6.82 (d, J = 6.8 Hz, 1 H), 7.08 (d, J = 7.7 Hz, 1 H), 7.13 (t, J = 5.3 Hz, 1 H), 7.32 (dd, J = 8.4, 7.3 Hz, 1 H) |
| 20 | 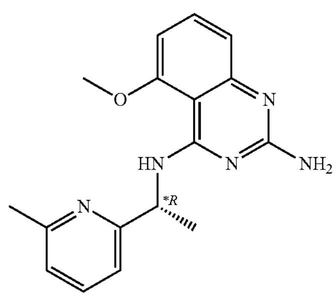 [SMILES: COc1cccc2nc(N)nc(N[C@H](C)c3cccc(C)n3)c12] | ¹H NMR (400 MHz, DMSO-d₆) δ ppm 1.49 (d, J = 6.6 Hz, 3 H), 2.58 (s, 3 H), 4.02 (s, 3 H), 5.37 (quin, J = 6.6 Hz, 1 H), 6.02 (s, 2 H), 6.56-6.62 (m, 1 H), 6.81 6 (dd, J = 8.3, 0.8 Hz, 1 H), 7.20 (d, J = 7.5 Hz, 1 H), 7.24 (d, J = 7.7 Hz, 1 H), 7.37 (t, J = 8.1 Hz, 1 H), 7.70 (t, J = 7.7 Hz, 1 H), 9.21 (d, J = 6.8 Hz, 1 H) |
| 21 | 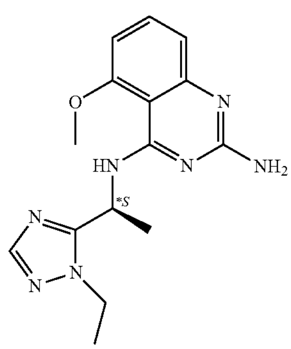 [SMILES: CCn1ncnc1[C@H](C)Nc1nc(N)nc2cccc(OC)c12] | ¹H NMR (400 MHz, DMSO-d₆) δ ppm 1.36 (t, J = 7.3 Hz, 3 H), 1.57 (d, J = 6.8 Hz, 3 H), 3.95 (s, 3 H), 4.21- 4.42 (m, 2 H), 5.65 (quin, J = 7.0 Hz, 1 H), 6.08 (br. s., 2 H), 6.58 (dd, J = 7.9, 0.7 Hz, 1 H), 6.81 (dd, J = 8.4, 0.7 Hz, 1 H), 7.39 (t, J = 8.1 Hz, 1 H), 7.88 (s, 1 H), 8.26 (d, J = 7.7 Hz, 1 H) |
| 22 | 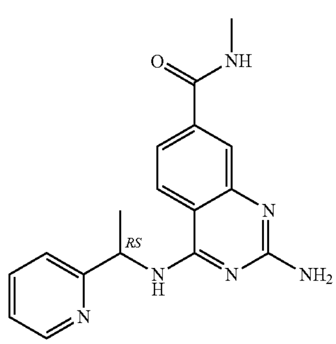 [SMILES: CNC(=O)c1ccc2c(NC(C)c3ccccn3)nc(N)nc2c1] | ¹H NMR (400 MHz, DMSO-d₆) δ ppm 1.60 (d, J = 7.3 Hz, 3 H), 2.80 (d, J = 4.4 Hz, 3 H), 5.60 (quin, J = 7.3 Hz, 1 H), 6.11 (s, 2 H), 7.24 (ddd, J = 7.4, 4.8, 1.0 Hz, 1 H), 7.45 (dt, J = 8.4, 1.8 Hz, 2 H), 7.65 (d, J = 1.8 Hz, 1 H), 7.73 (td, J = 7.7, 1.8 Hz, 1 H), 8.16 (d, J = 7.9 Hz, 1 H), 8.25 (d, J = 8.4 Hz, 1 H), 8.49-8.56 (m, 2 H) |

TABLE II-continued

Compounds of formula (I). The following compounds were synthesized according to one of the methods described above.

| # | STRUCTURE | H NMR |
|---|---|---|
| 23 | 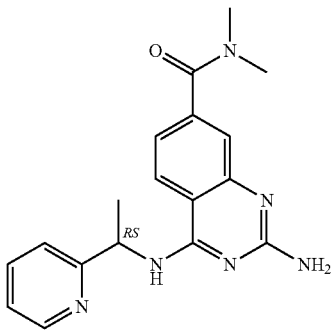 | $^1$H NMR (400 MHz, DMSO-d$_6$) δ ppm 1.60 (d, J = 7.0 Hz, 3 H), 2.91 (s, 3 H), 3.00 (s, 3 H), 5.61 (quin, J = 7.3 Hz, 1 H), 6.12 (s, 2 H), 7.02 (dd, J = 8.3, 1.7 Hz, 1 6 H), 7.12 (d, J = 1.5 Hz, 1 H), 7.24 (ddd, J = 7.5, 4.8, 0.9 Hz, 1 H), 7.44 (d, J = 7.9 Hz, 1 H), 7.73 (td, J = 7.7, 1.8 Hz, 1 H), 8.16 (d, J = 7.9 Hz, 1 H), 8.24 (d, J = 8.4 Hz, 1 H), 8.51-8.56 (m, 1 H) |
| 24 | 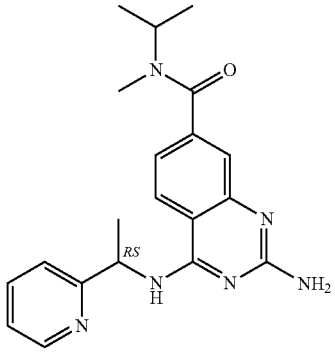 [SMILES: CC(Nc1nc(N)nc2cc(C(=O)N(C)C(C)C)ccc12)c1ccccn1] | $^1$H NMR (400 MHz, DMSO-d$_6$) δ ppm 1.03-1.20 (m, 6 H), 1.60 (d, J = 7.0 Hz, 3 H), 2.68-2.89 (m, 3 H), 3.76-3.91 (m, 1 H), 5.61 (quin, J = 7.2 Hz, 1 H), 6.13 (br. s., 2 H), 6.94-7.02 (m, 1 H), 7.02-7.12 (m, 1 H), 7.24 (ddd, J = 7.4, 4.8, 1.0 Hz, 1 H), 7.44 (s, 1 H), 7.73 (td, J = 7.7, 2.0 Hz, 1 H), 8.15 (s, 1 H), 8.23 (s, 1 H), 8.50-8.57 (m, 1 H) |
| 25 | 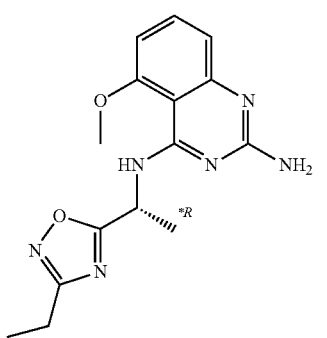 [SMILES: CCc1noc([C@@H](C)Nc2nc(N)nc3cccc(OC)c23)n1] | $^1$H NMR (400 MHz, DMSO-d$_6$) δ ppm 1.23 (t, J = 7.5 Hz, 3 H), 1.68 (d, J = 7.0 Hz, 3 H), 2.71 (q, J = 7.6 Hz, 2 H), 3.96 (s, 3 H), 5.71 (quin, J = 7.2 Hz, 1 H), 6.05 (br. s., 2 H), 6.57-6.62 (m, 1 H), 6.83 (dd, J = 8.5, 0.8 Hz, 1 H), 7.41 (t, J = 8.1 Hz, 1 H), 8.31 (d, J = 7.5 Hz, 1 H) |
| 26 | 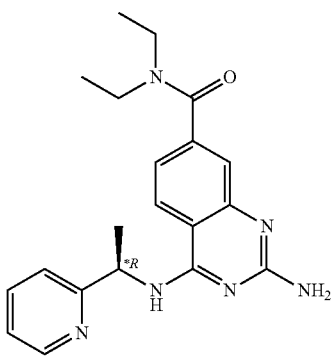 [SMILES: CCN(CC)C(=O)c1ccc2c(N[C@H](C)c3ccccn3)nc(N)nc2c1] | $^1$H NMR (400 MHz, DMSO-d$_6$) δ ppm 1.05 (br. s., 3 H), 1.16 (br. s., 3 H), 1.60 (d, J = 7.0 Hz, 3 H), 3.20 (br. s., 2 H), 3.43 (br. s., 2 H), 5.60 (quin, J = 7.3 Hz, 1 H), 6.11 (s, 2 H), 6.97 (dd, J = 8.3, 1.7 Hz, 1 H), 7.05 (d, J = 1.3 Hz, 1 H), 7.24 (ddd, J = 7.4, 4.8, 1.0 Hz, 1 H), 7.45 (d, J = 7.9 Hz, 1 H), 7.73 (td, J = 7.6, 1.9 Hz, 1 H), 8.15 (d, J = 7.9 Hz, 1 H), 8.24 (d, J = 8.4 Hz, 1 H), 8.50 - 8.56 (m, 1 H) |

TABLE II-continued

Compounds of formula (I). The following compounds were synthesized according to one of the methods described above.

| # | STRUCTURE | H NMR |
|---|---|---|
| 27 | 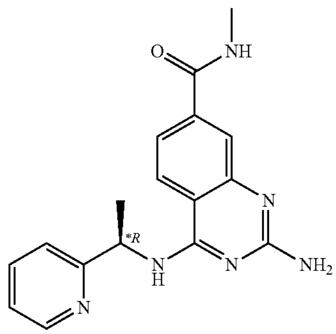 [SMILES: CNC(=O)c1ccc2c(N[C@H](C)c3ccccn3)nc(N)nc2c1] | $^1$H NMR (400 MHz, DMSO-d$_6$) δ ppm 1.60 (d, J = 7.0 Hz, 3 H), 2.79 (d, J = 4.4 Hz, 3 H), 5.60 (quin, J = 7.3 Hz, 1 H), 6.09 (s, 2 H), 7.24 (ddd, J = 7.4, 4.8, 1.0 Hz, 1 H), 7.41-7.48 (m, 2 H), 7.65 (d, J = 1.5 Hz, 1 H), 7.73 (td, J = 7.7, 2.0 Hz, 1 H), 8.15 (d, J = 7.9 Hz, 1 H), 8.24 (d, J = 8.6 Hz, 1 H), 8.48-8.56 (m, 2 H) |
| 28 | 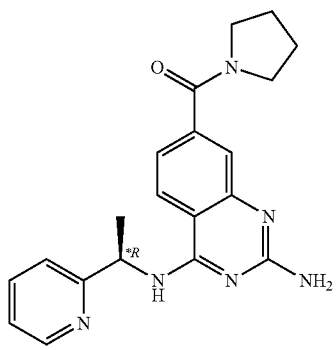 [SMILES: C[C@@H](Nc1nc(N)nc2cc(C(=O)N3CCCC3)ccc12)c1ccccn1] | $^1$H NMR (400 MHz, DMSO-d$_6$) δ ppm 1.60 (d, J = 7.0 Hz, 3 H), 1.76-1.93 (m, 4 H), 3.37 (t, J = 6.5 Hz, 2 H), 3.47 (t, J = 6.8 Hz, 2 H), 5.60 (quin, J = 7.2 Hz, 1 H), 6.10 (s, 2 H), 7.12 (dd, J = 8.3, 1.7 Hz, 1 H), 7.22 (d, J = 1.5 Hz, 1 H), 7.23-7.26 (m, 1 H), 7.44 (d, J = 7.9 Hz, 1 H), 7.73 (td, J = 7.7, 1.8 Hz, 1 H), 8.15 (d, J = 7.9 Hz, 1 H), 8.23 (d, J = 8.6 Hz, 1 H), 8.50-8.56 (m, 1 H) |
| 29 | 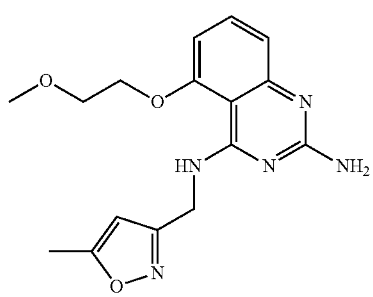 [SMILES: COCCOc1cccc2nc(N)nc(NCc3cc(C)on3)c12] | $^1$H NMR (400 MHz, DMSO-d$_6$) δ ppm 2.33-2.42 (m, 3 H) 3.27 (s, 3 H) 3.64-3.80 (m, 2 H) 4.16-4.31 (m, 2 H) 4.69 (d, J = 5.50 Hz, 2 H) 6.12 (s, 2 H) 6.21-6.29 (m, 1 H) 6.59 (d, J = 7.48 Hz, 1 H) 6.82 (d, J = 7.70 Hz, 1 H) 7.37 (t, J = 8.25 Hz, 1 H) 8.37 (s, 1 H) |
| 30 | 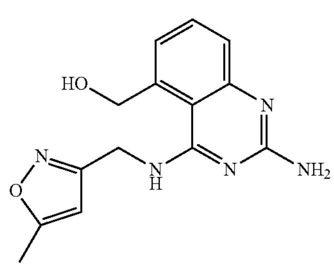 [SMILES: Cc1cc(CNc2nc(N)nc3cccc(CO)c23)no1] | $^1$H NMR (400 MHz, DMSO-d$_6$) δ ppm 0.87 (t, J = 7.26 Hz, 3 H) 1.23-1.38 (m, 2 H) 1.38-1.49 (m, 2 H) 1.54 (d, J = 7.04 Hz, 3 H) 3.33-3.50 (m, 2 H) 5.38 (t, J = 7.26 Hz, 1 H) 6.10 (s, 2 H) 7.05 (dd, J = 7.04, 1.32 Hz, 1 H) 7.30 (dd, J = 8.47, 1.21 Hz, 1 H) 7.48 (dd, J = 8.36, 7.04 Hz, 1 H) 7.53 (dd, J = 1.87, 0.77 Hz, 1 H) 7.68 (t, J = 4.73 Hz, 1 H) 9.09 (d, J = 1.98 Hz, 1 H) 9.39 (d, J = 8.14 Hz, 1 H) |

TABLE II-continued

Compounds of formula (I). The following compounds were synthesized according to one of the methods described above.

| # | STRUCTURE | H NMR |
|---|-----------|-------|
| 31 | (structure) | $^1$H NMR (400 MHz, DMSO-$d_6$) δ ppm 2.28-2.40 (m, 3 H) 3.90 (s, 3 H) 4.71 (d, J = 5.94 Hz, 2 H) 6.21 (d, J = 0.88 Hz, 1 H) 6.33 (br. s., 2 H) 6.46 (dd, J = 8.80, 3.52 Hz, 1 H) 7.26 (dd, J = 10.89, 8.69 Hz, 1 H) 8.49 (t, J = 5.72 Hz, 1 H) |
| 32 | (structure) | Not available |

SFC Purification Methods.
General Procedure

The Supercritical Fluid Chromatography (SFC) separation was performed with supercritical $CO_2$ and a modifier as specified in the table using a column as specified in the table.

TABLE III

Compounds of formula (I). The following compounds were isolated SFC seperation.

| # | Column | Modifier |
|---|--------|----------|
| 1 | Chiralpak Diacel AS 20 × 250 mm | iPrOH with 0.2% iPrNH2 |
| 2 | Chiralpak Diacel AS 20 × 250 mm | MeOH with 0.2% iPrNH2 |
| 3 | Chiralpak Diacel AS 20 × 250 mm | iPrOH with 0.2% iPrNH2 |
| 4 | Chiralpak Diacel AD 30 × 250 mm | iPrOH with 0.2% iPrNH2 |
| 5 | Chiralpak Diacel AS 20 × 250 mm | iPrOH with 0.4% iPrNH2 |
| 6 | Chiralpak Diacel AS 20 × 250 mm | EtOH with 0.2% iPrNH2 |
| 7 | Chiralpak Diacel AS 20 × 250 mm | iPrOH with 0.2% iPrNH2 |
| 8 | Chiralpak Diacel AS 20 × 250 mm | iPrOH with 0.2% iPrNH2 |
| 9 | Chiralpak Diacel AD 30 × 250 mm | EtOH with 0.2% iPrNH2 |
| 10 | Chiralpak Diacel AS 20 × 250 mm | EtOH with 0.4%iPrNH2 |
| 16 | Chiralpak Diacel AD 30 × 250 mm | EtOH with 0.2% iPrNH2 |
| 18 | Chiralpak Diacel AS 20 × 250 mm | iPrOH with 0.2% iPrNH2 |
| 20 | Chiralpak Diacel AS 20 × 250 mm | EtOH with 0.2% iPrNH2 |
| 21 | Chiralpak Diacel AD 30 × 250 mm | EtOH with 0.2% iPrNH2 |
| 25 | Chiralpak Diacel AD 30 × 250 mm | MeOH with 0.4% iPrNH2 |
| 26 | Chiralpak Diacel AD 30 × 250 mm | EtOH with 0.2% iPrNH2 |
| 27 | Chiralpak Diacel AD 30 × 250 mm | MeOH with 0.4% iPrNH2 |
| 28 | Chiralpak Diacel AD 30 × 250 mm | EtOH with 0.4% iPrNH2 |

For all compounds the first eluting compound was assigned as *R.

*R means an enantiomeric pure configuration of which the absolute stereochemistry is unknown.

Analytical Methods.
General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+HCOO]$^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

TABLE IV

LCMS Method codes (Flow expressed in mL/min; column temperature (T) in °C., Run time in minutes).

| Method code | Instrument | Column | Mobile phase | gradient | Flow Column T | Run time |
|---|---|---|---|---|---|---|
| B7010 B7014 | Waters: Acquity ® UPLC ®- DAD and SQD | Waters: HSS T3 (1.8 µm, 2.1*100 mm) | A: 95% $CH_3COONH_4$ 10 mM + 5% $CH_3CN$ B: $CH_3CN$ | From 100% A to 5% A in 2.10 min, to 0% A in 0.90 min, to 5% A in 0.5 min | 0.8 55 | 3.5 |
| B8011 B8002 | Waters: Acquity ® UPLC ®- DAD and SQD | Waters: BEH C18 (1.7 µm, 2.1*50 mm) | A: 95% $CH_3COONH_4$ 10 mM + 5% $CH_3CN$ B: $CH_3CN$ | From 95% A to 5% A in 1.3 min, held for 0.7 min. | 0.8 55 | 2 |
| B9007 B9008 | Waters: Acquity ® UPLC ®- DAD and SQD | Waters: HSS T3 (1.8 µm, 2.1*100 mm) | A: 95% $CH_3COONH_4$ 10 mM + 5% $CN_3CH$ B: $CH_3CN$ | From 100% A to 5% A in 2.10 min, to 0% A in 0.90 min, to 5% A in 0.5 min | 0.8 55 | 3.5 |

TABLE V

Compounds of formula (I). The following compounds were characterized according to one of the methods described above.

| # | Method code | Retention Time (min) | Mass Found (M + H) |
|---|---|---|---|
| 1 | B701067014 | 0.61 | 266 |
| 2 | B701067014 | 1.59 | 296 |
| 3 | B9007B9008 | 1.61 | 350 |
| 4 | B8011B8002 | 0.69 | 284 |
| 5 | B701067014 | 1.39 | 280 |
| 6 | B701067014 | 1.31 | 296 |
| 7 | B8011B8002 | 0.78 | 300 |
| 8 | B9007B9008 | 1.32 | 324 |
| 9 | B9007B9008 | 1.29 | 284 |
| 10 | B9007B9008 | 1.31 | 302 |
| 11 | B8011B8002 | 0.69 | 274 |
| 12 | B701067014 | 1.26 | 286 |
| 13 | B8011B8002 | 0.64 | 274 |
| 14 | B701067014 | 1.32 | 274 |
| 15 | B8011B8002 | 0.77 | 325 |
| 16 | B8011B8002 | 0.62 | 299 |
| 17 | B8011138002 | 0.53 | 311 |
| 18 | B8011138002 | 0.79 | 284 |
| 19 | B8011138002 | 0.65 | 270 |
| 20 | B8011138002 | 0.84 | 310 |
| 21 | B8011138002 | 0.61 | 314 |
| 22 | B8011138002 | 0.56 | 323 |
| 23 | B8011138002 | 0.59 | 337 |
| 24 | B8011138002 | 0.70 | 365 |
| 25 | B8011138002 | 0.75 | 315 |
| 26 | B8011138002 | 0.69 | 365 |
| 27 | B8011138002 | 0.56 | 323 |
| 28 | B8011138002 | 0.66 | 363 |
| 29 | B8011138002 | 0.70 | 330 |
| 30 | B9007139008 | 1.04 | 286 |
| 31 | B9007139008 | 1.36 | 304 |
| 32 | B9007139008 | 1.46 | 348 |

Biological Activity of Compounds of Formula (I)
Description of Biological Assays
Assessment of TLR7 and TLR8 Activity The ability of compounds to activate human TLR7 and/or TLR8 was assessed in a cellular reporter assay using HEK293 cells transiently transfected with a TLR7 or TLR8 expression vector and NFκB-luc reporter construct.

Briefly, HEK293 cells were grown in culture medium (DMEM supplemented with 10% FCS and 2 mM Glutamine). For transfection of cells in 15 cm dishes, cells were detached with Trypsin-EDTA, transfected with a mix of CMV-TLR7 or TLR8 plasmid (1700 ng), NFκB-luc plasmid (850 ng) and a transfection reagent and incubated for 48 h at 37° C. in a humidified 5% $CO_2$ atmosphere. Transfected cells were then washed in PBS, detached with Trypsin-EDTA and resuspended in medium to a density of $1.25 \times 10^5$ cells/mL. Forty microliters of cells were then dispensed into each well in 384-well plates, where 200 nL of compound in 100% DMSO was already present. Following 6 hours incubation at 37° C., 5% $CO_2$, the luciferase activity was determined by adding 15 µL of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

Compound toxicity was determined in parallel using a similar dilution series of compound with 40 µL per well of cells transfected with the CMV-TLR7 construct alone ($1.25 \times 10^5$ cells/mL), in 384-well plates. Cell viability was measured after 6 hours incubation at 37° C., 5% $CO_2$ by adding 15 µL of ATP lite (Perkin Elmer) per well and reading on a ViewLux ultraHTS microplate imager (Perkin Elmer). Data was reported as $CC_{50}$.

In parallel, a similar dilution series of compound was used (200 nL of compound in 100% DMSO) with 40 µL per well of cells transfected with NFκB-luc reporter construct alone ($1.25 \times 10^5$ cells/mL). Six hours after incubation at 37° C., 5% $CO_2$, the luciferase activity was determined by adding 15 µl of Steady Lite Plus substrate (Perkin Elmer) to each well and readout performed on a ViewLux ultraHTS microplate imager (Perkin Elmer). Counterscreen data is reported as LEC.

Activation of ISRE Promoter Elements

The potential of compounds to induce IFN-I was also evaluated by measuring the activation of interferon-stimulated responsive elements (ISRE) by conditioned media from PBMC. The ISRE element of sequence GAAACT-GAAACT (SEQ ID: 1) is highly responsive to the STAT1-

STAT2-IRF9 transcription factor, activated upon binding of IFN-I to their receptor IFNAR (Clontech, PT3372-5W). The plasmid pISRE-Luc from Clontech (ref. 631913) contains 5 copies of this ISRE element, followed by the firefly luciferase ORF. A HEK293 cell line stably transfected with pISRE-Luc (HEK-ISREluc) was established to profile the conditioned PBMC cell culture media.

Briefly, PBMCs were prepared from buffy coats of at least two donors using a standard Ficoll centrifugation protocol. Isolated PBMCs were resuspended in RPMI medium supplemented with 10% human AB serum and $2\times10^5$ cells/well were dispensed into 384-well plates containing compounds (70 μL total volume). After overnight incubation, 10 μL of supernatant was transferred to 384-well plates containing $5\times10^3$ HEK-ISREluc cells/well in 30 μL (plated the day before). Following 24 hours of incubation, activation of the ISRE elements was measured by assaying luciferase activity using 40 μL/well Steady Lite Plus substrate (Perkin Elmer) and measured with ViewLux ultraHTS microplate imager (Perkin Elmer). The stimulating activity of each compound on the HEK-ISREluc cells was reported as LEC value, defined as the compound concentration applied to the PBMCs resulting in a luciferase activity at least two fold above the standard deviation of the assay. The LEC in turn indicates the degree of ISRE activation on transfer of a defined amount of PBMC culture medium. Recombinant interferon α-2a (Roferon-A) was used as a standard control compound.

TABLE VI

| | BIOLOGICAL ACTIVITY | | |
|---|---|---|---|
| # | Human TLR 7 (LEC) μM | Human TLR 8 (LEC) μM | HEK-ISRE luc (LEC) μM |
| 1 | 0.72 | >25 | 0.61 |
| 2 | 0.94 | >25 | 0.49 |
| 3 | 0.76 | >25 | 0.47 |
| 4 | 0.92 | 19.8 | 0.59 |
| 5 | 0.53 | 14.7 | 0.11 |
| 6 | 3.75 | >25 | 0.64 |
| 7 | 0.82 | 16.4 | 0.38 |
| 8 | 4.94 | NA | 2.11 |
| 9 | 5.21 | >25 | 1.68 |
| 10 | 0.42 | 12.3 | 0.11 |
| 11 | 0.45 | 3.09 | 0.082 |
| 12 | 0.047 | 1.94 | 0.036 |
| 13 | 0.46 | 5.22 | 0.12 |
| 14 | 0.65 | >25 | 0.13 |
| 15 | 0.61 | >25 | 0.56 |
| 16 | 2.44 | 9.14 | 0.55 |
| 17 | 0.83 | 5.51 | 0.16 |
| 18 | 8.25 | 24.3 | 7.83 |
| 19 | 0.11 | 1.74 | 0.051 |
| 20 | 1.46 | >25 | 0.62 |
| 21 | 6.1 | 8.85 | 0.54 |
| 22 | 14.7 | >25 | 2.20 |
| 23 | 6.67 | >25 | 1.62 |
| 24 | 14.3 | 11.0 | 1.75 |
| 25 | 1.95 | 6.62 | 0.49 |
| 26 | 2.14 | >25 | 7.33 |
| 27 | 8.24 | >25 | 5.04 |
| 28 | 2.24 | >25 | 1.57 |
| 29 | 0.082 | 8.15 | NA |
| 30 | 0.63 | 9.0 | 0.14 |
| 31 | 0.74 | >25 | 0.46 |
| 32 | NA | NA | NA |

NA = not available.
All compounds showed no toxicity up to the highest tested concentration.
All compounds showed no activity (LEC >25 μM) in the HEK 293 NF-kB counterscreen assay described above.

The invention claimed is:

1. A method of treating a viral infection in which the modulation of TLR7 and/or TLR8 is involved in a subject in need thereof, the method comprising administering to the subject a therapeutically effective amount of a compound of formula (I)

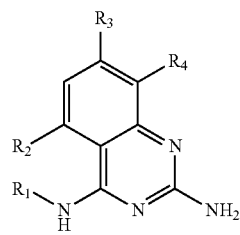

or a pharmaceutically acceptable salt thereof, wherein $R_1$ is selected from the group consisting of:

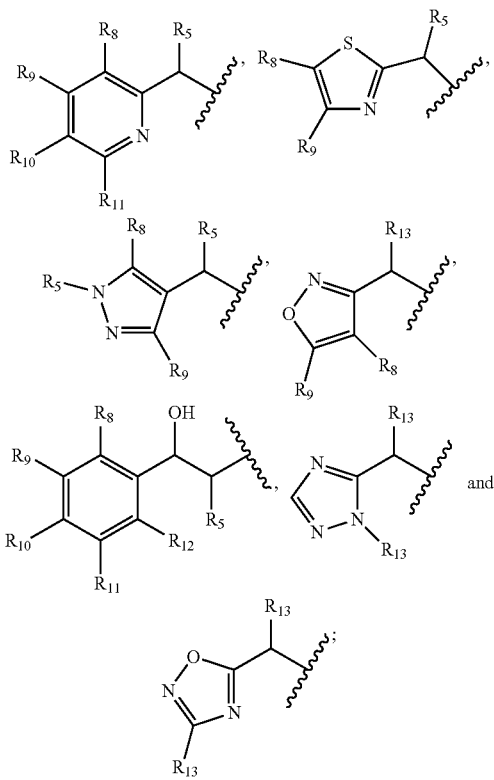

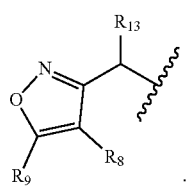

$R_2$ is selected from the group consisting of hydrogen, —O—$(C_{1-3})$-alkyl, halogen, $(C_{1-3})$-alkyl, —O—$(C_{1-3})$-alkyl-O—$(C_{1-3})$-alkyl and $CH_2OH$;

$R_3$ is selected from the group consisting of hydrogen, —O—$(C_{1-3})$-alkyl, halogen, $(C_{1-3})$-alkyl and C(=O)—$R_7$, wherein $R_7$ is selected from the group consisting of —O—$(C_{1-3})$-alkyl, $NH_2$, $NH(CH_3)$, $N(CH_3)_2$, $N(CH_3)(C_{1-3})$-alkyl, $N((C_{1-3})$-alkyl$)_2$ and pyrolidine;

$R_4$ is hydrogen or fluorine;

$R_5$ is selected from the group consisting of $(C_{1-3})$-alkyl, $(C_{1-3})$-fluoro-alkyl, and $CH_2OH$;

$R_8$, $R_9$, $R_{10}$, $R_{11}$ and $R_{12}$ are each independently selected from the group consisting of hydrogen, $(C_{1-3})$-alkyl, —O—$(C_{1-3})$-alkyl and halogen; and $R_{13}$ is selected from the group consisting of hydrogen, $(C_{1-3})$-alkyl and $(C_{1-3})$-fluoro-alkyl.

2. The method of claim 1, wherein $R_5$ is $CH_3$, and $R_9$ and $R_{11}$ are each independently H or $CH_3$.

3. The method of claim 1, wherein $R_{13}$ is H, $CH_3$ or $CH_2CH_3$.

4. The method of claim 1, wherein $R_1$ is

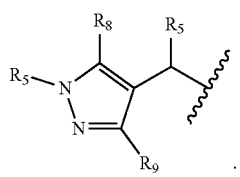

5. The method of claim 4, wherein $R_9$ is $CH_3$.

6. The method of claim 4, wherein $R_2$ is $OCH_3$ or —O—$C_2H_4$—O—$CH_3$.

7. The method of claim 4, wherein:
$R_3$, $R_4$, $R_{13}$ and $R_8$ are each H;
$R_9$ is $CH_3$; and
$R_2$ is —O—$(C_{1-3})$-alkyl-O—$(C_{1-3})$-alkyl.

8. The method of claim 4, wherein:
$R_3$, $R_4$, $R_{13}$ and $R_8$ are each H;
$R_9$ is $CH_3$; and
$R_2$ is $OCH_3$.

9. The method of claim 1, wherein $R_1$ is

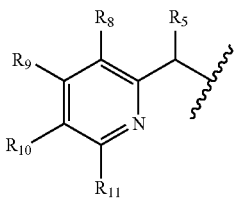

10. The method of claim 9, wherein
$R_5$ is $CH_3$; and
$R_8$, $R_9$, $R_{10}$ and $R_{11}$ are each H.

11. The method of claim 1, wherein $R_1$ is

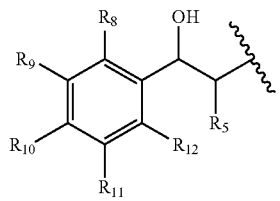

12. The method of claim 11, wherein $R_5$ is $CH_3$ or $CH_2OH$.

13. The method of claim 1, wherein $R_1$ is

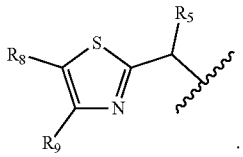

14. The method of claim 13, wherein:
$R_5$ is $CH_3$, and
$R_8$ and $R_9$ are each H.

15. The method of claim 1, wherein $R_1$ is

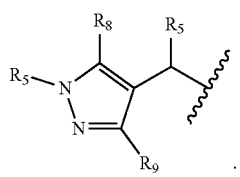

16. The method of claim 15, wherein
each $R_5$ is $CH_3$; and
$R_8$ and $R_9$ are each H.

17. The method of claim 4, wherein $R_1$ is
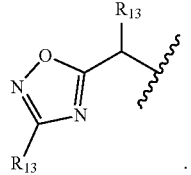
18. The method of claim 17, wherein each $R_{13}$ is $(C_{1-3})$-alkyl.
19. The method of claim 1, wherein $R_1$ is
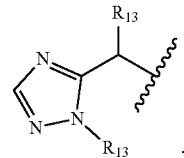
20. The method of claim 19, wherein each $R_{13}$ is $(C_{1-3})$-alkyl.
21. The method of claim 1, wherein the compound is selected from the group consisting of:
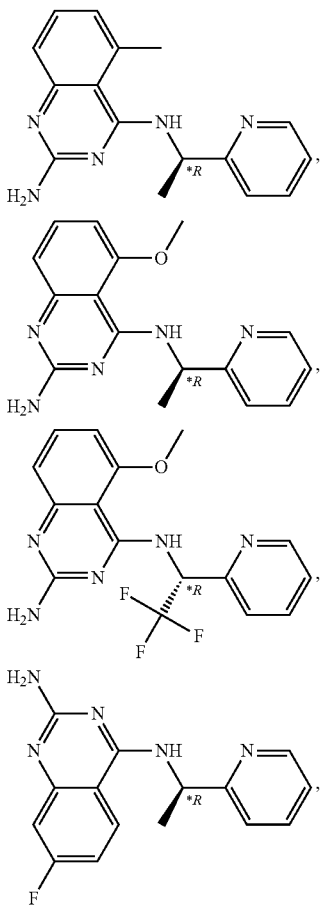
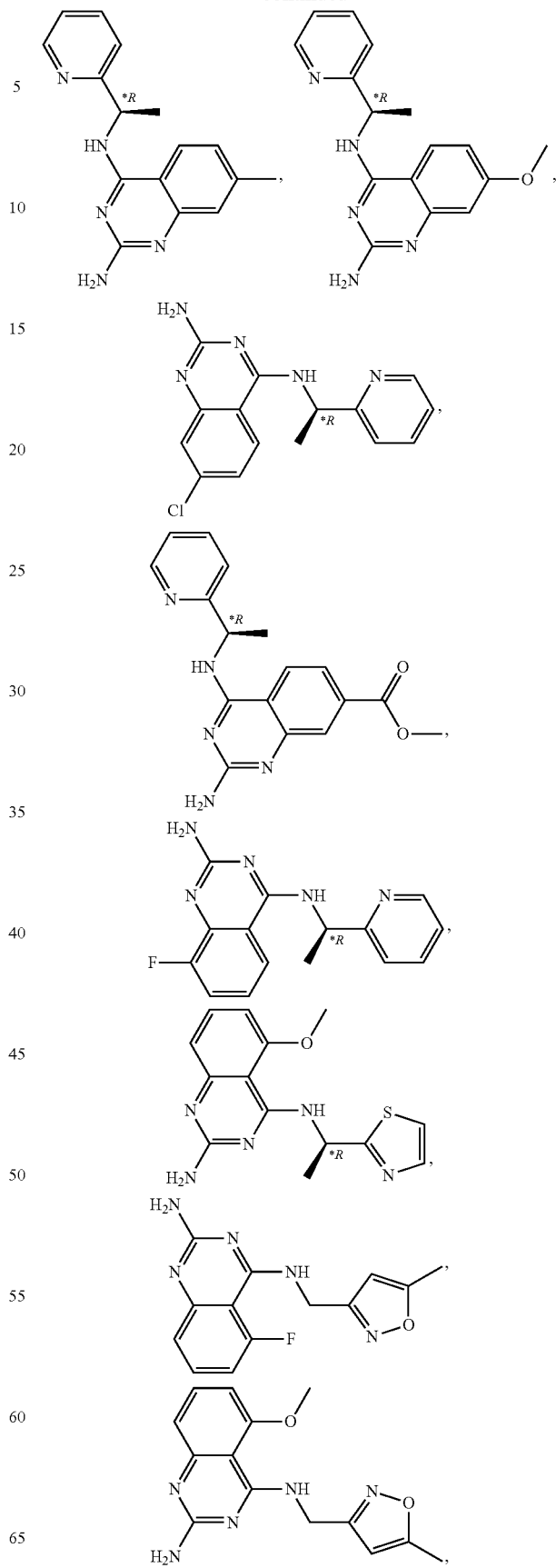

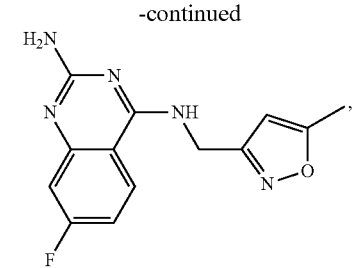
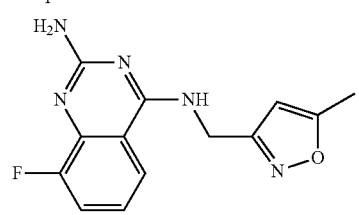
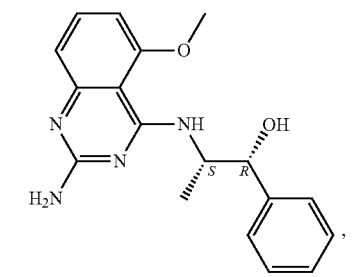
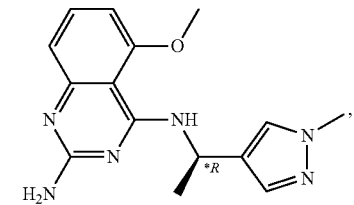
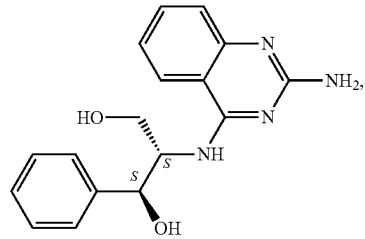
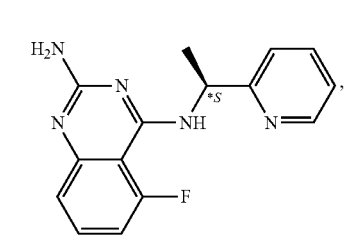
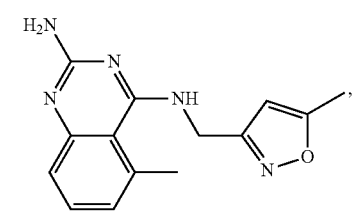
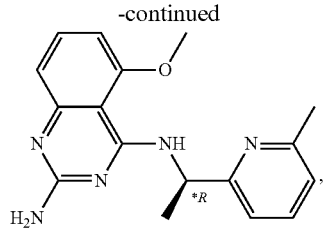
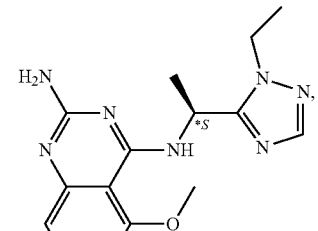
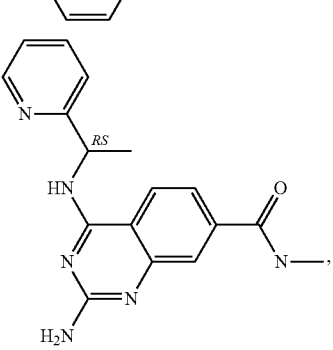
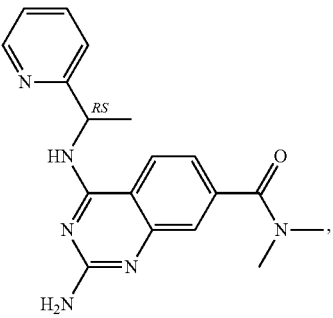
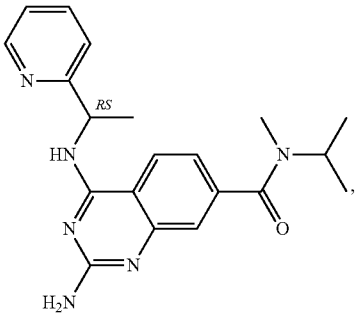
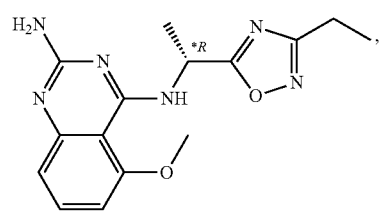

-continued

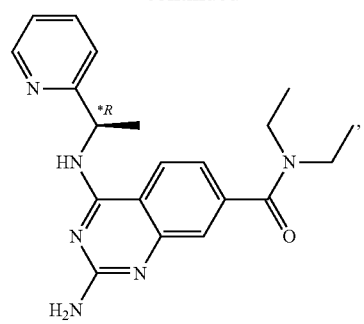

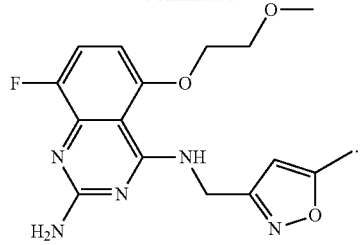

22. The method of claim 1, wherein the compound is together with one or more pharmaceutically acceptable excipients, diluents or carriers in a pharmaceutical composition.

23. The method of claim 1, wherein the treatment stimulates the innate immune system of the subject through activation of TLR7 and/or TLR8.

24. A method of modulating human TLR7 and/or TLR8 by contacting a cell with an effective amount of a compound of formula (I):

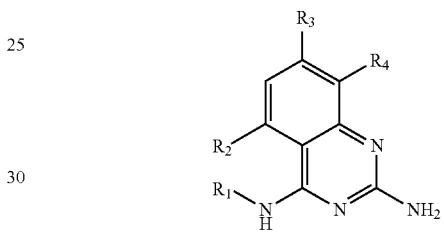

or a pharmaceutically acceptable salt thereof, wherein $R_1$ is selected from the group consisting of:

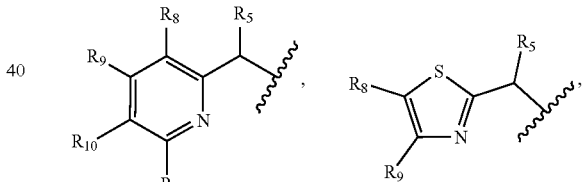

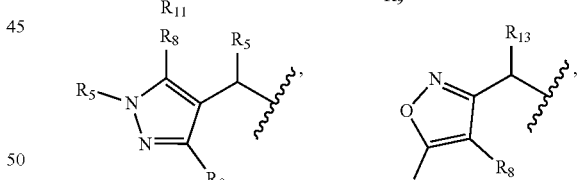

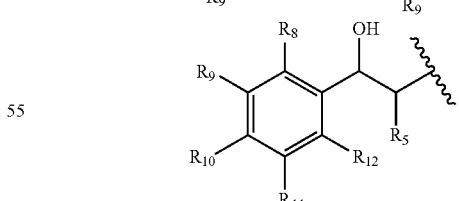

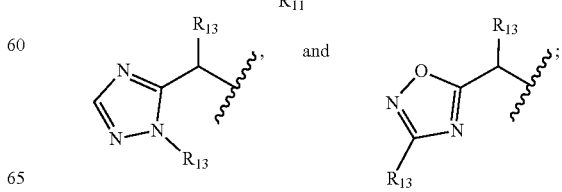

R2 is selected from the group consisting of hydrogen, —O—(C1-3)-alkyl, halogen, (C1-3)-alkyl, —O—(C1-3)-alkyl-O—(C1-3)-alkyl and CH2OH;

R3 is selected from the group consisting of hydrogen, —O—(C1-3)-alkyl, halogen, (C1-3)-alkyl and C(=O)—R7, wherein R7 is selected from the group consisting of —O—(C1-3)-alkyl, NH2, NH(CH3), N(CH3)2, N(CH3)(C1-3)-alkyl, N(C1-3)-alkyl2 and pyrolidine;

R4 is hydrogen or fluorine;

R5 is selected from the group consisting of (C1-3)-alkyl, (C1-3)-fluoro-alkyl, and CH2OH;

R8, R9, R10, R11 and R12 are each independently selected from the group consisting of hydrogen, (C1-3)-alkyl, —O—(C1-3)-alkyl and halogen; and R13 is selected from the group consisting of hydrogen, (C1-3)-alkyl and (C1-3)-fluoro-alkyl.

25. The method of claim 24, wherein the compound is selected from the group consisting of:

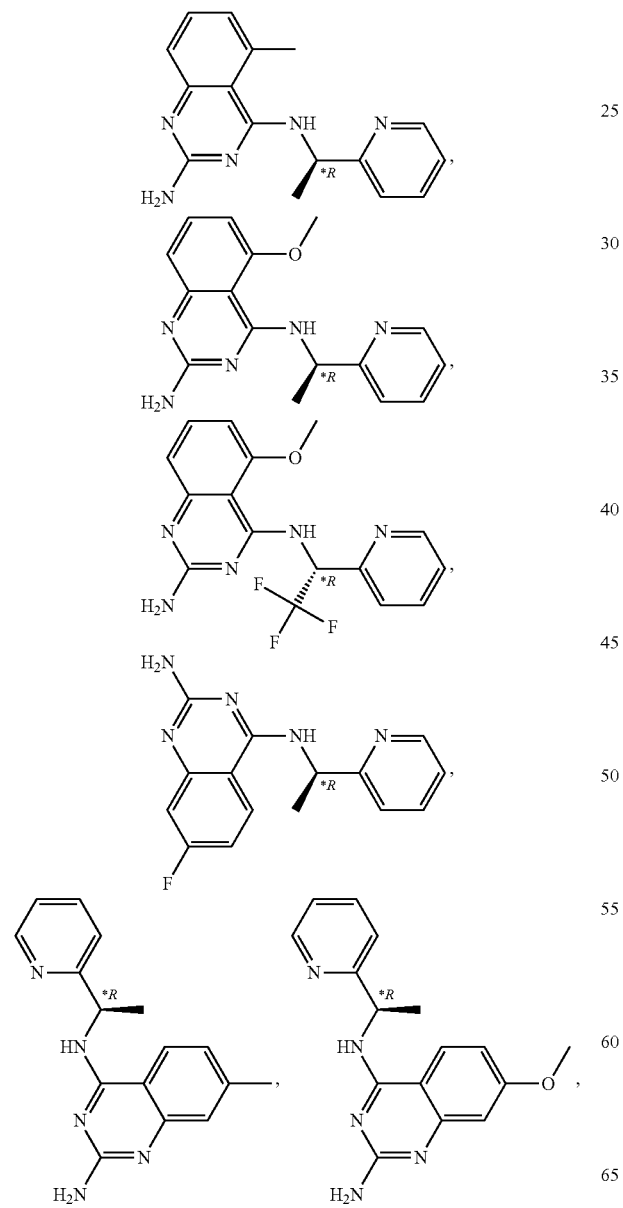

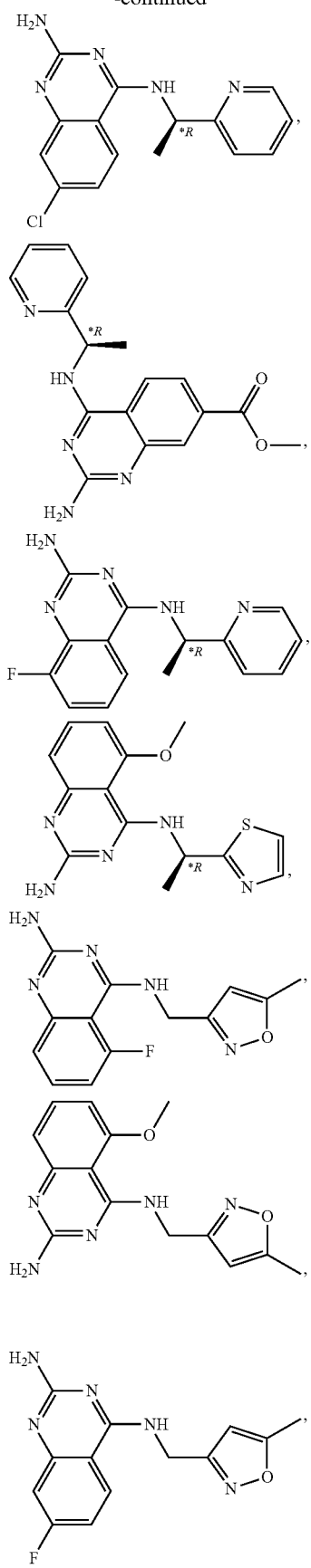

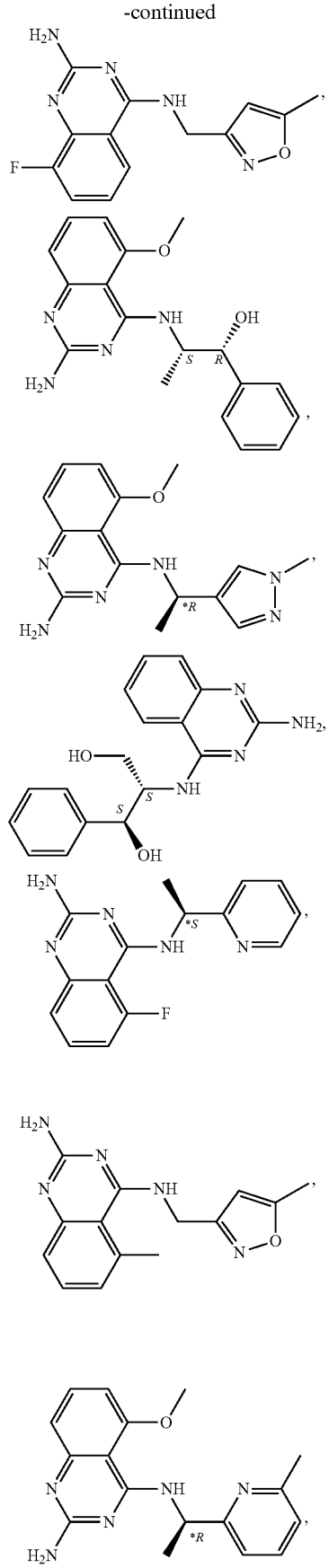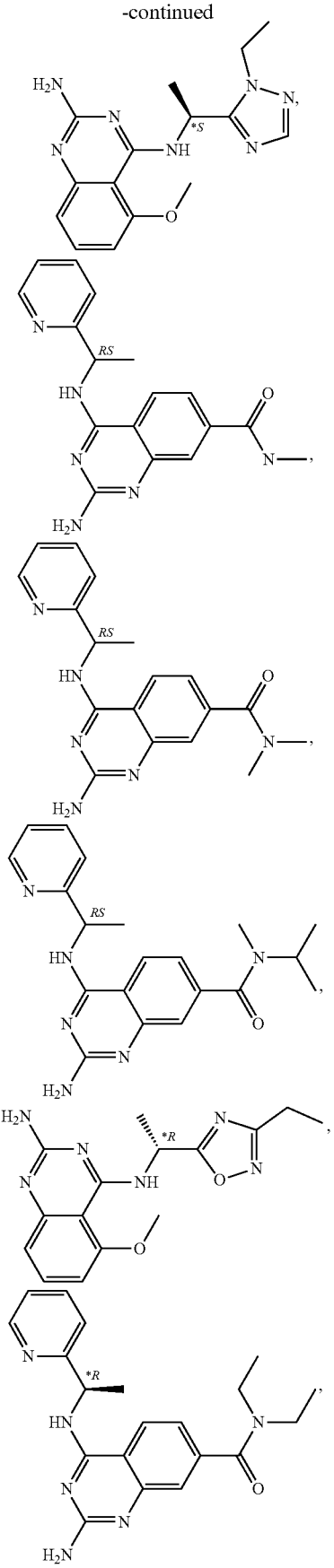

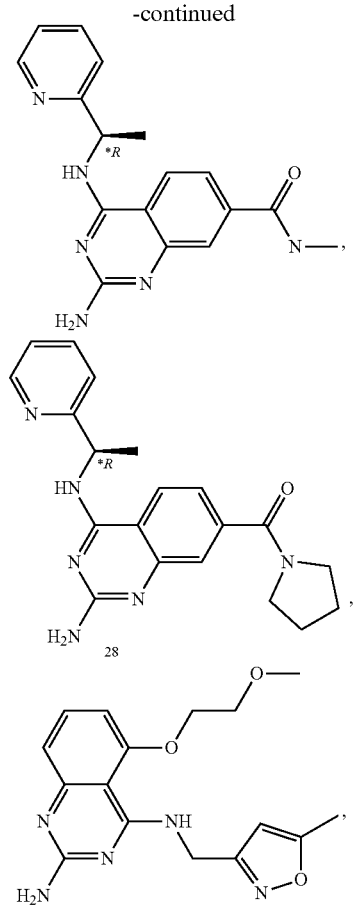
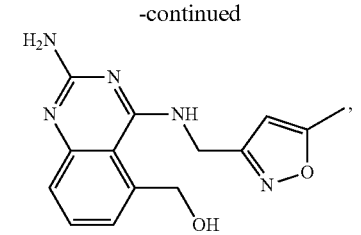
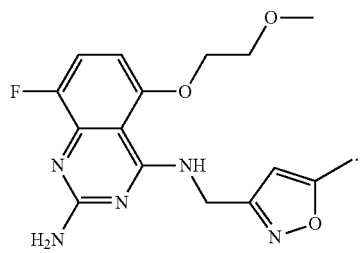
26. The method of claim 24, wherein the compound is together with one or more pharmaceutically acceptable excipients, diluents or carriers in a pharmaceutical composition.
* * * * *

SEQUENCE LISTING

```
<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaaactgaaa ct                                                          12
```